US006797482B2

(12) United States Patent
Woods, Jr.

(10) Patent No.: US 6,797,482 B2
(45) Date of Patent: *Sep. 28, 2004

(54) METHODS FOR THE HIGH-RESOLUTION IDENTIFICATION OF SOLVENT-ACCESSIBLE AMIDE HYDROGENS IN PROTEIN BINDING SITES

(75) Inventor: Virgil L. Woods, Jr., San Diego, CA (US)

(73) Assignee: ExSAR Corporation, Monmouth Junction, NJ (US)

( * ) Notice: Subject to any disclaimer, the term of this patent is extended or adjusted under 35 U.S.C. 154(b) by 111 days.

This patent is subject to a terminal disclaimer.

(21) Appl. No.: 09/954,376

(22) Filed: Sep. 10, 2001

(65) Prior Publication Data

US 2002/0042080 A1 Apr. 11, 2002

Related U.S. Application Data

(62) Division of application No. 08/919,187, filed on Aug. 19, 1997, now Pat. No. 6,291,189, which is a continuation-in-part of application No. 08/895,330, filed on Jul. 16, 1997, now Pat. No. 6,331,400, which is a continuation of application No. 08/240,593, filed on May 10, 1994, now Pat. No. 5,658,739.

(51) Int. Cl.[7] .......................... G01N 33/53; C12Q 1/37

(52) U.S. Cl. ........................ 435/7.1; 435/23; 435/24; 436/501; 436/536; 436/86; 436/89; 436/161; 436/173; 436/174; 436/175

(58) Field of Search ......................... 435/7.1, 23–4; 436/501, 536, 86, 89, 161, 173–175

(56) References Cited

U.S. PATENT DOCUMENTS

| | | | |
|---|---|---|---|
| 3,560,158 A | 2/1971 | Banson | 23/230 |
| 3,623,840 A | 11/1971 | Benson | 23/230 |
| 3,828,102 A | 8/1974 | Fromageot et al. | 424/1 |
| 4,153,416 A | 5/1979 | Bonner et al. | 23/230 |
| 4,517,686 A | 5/1985 | Ruoslahti et al. | 3/1 |
| 4,578,079 A | 3/1986 | Ruoslahti et al. | 623/11 |
| 4,589,881 A | 5/1986 | Pierschbacher et al. | 623/11 |
| 4,614,517 A | 9/1986 | Ruoslahti et al. | 623/11 |
| 4,661,111 A | 4/1987 | Ruoslahti et al. | 623/11 |
| 4,792,525 A | 12/1988 | Ruoslahti et al. | 435/240.243 |
| 4,956,303 A | 9/1990 | Self | 436/542 |
| 4,963,263 A | 10/1990 | Kauvar | 210/635 |
| 5,030,565 A | 7/1991 | Niman et al. | 435/70.21 |
| 5,273,886 A | 12/1993 | Aswad | 435/15 |
| 5,470,753 A | 11/1995 | Sepetov et al. | 436/89 |
| 5,658,739 A | * 8/1997 | Woods, Jr. | 435/7.1 |
| 5,792,664 A | 8/1998 | Chait et al. | 436/89 |

FOREIGN PATENT DOCUMENTS

EP  0 529 604 A1  3/1993

OTHER PUBLICATIONS

Anderegg and Wagner, 1995, "Mass spectrometric characterization of a protein–ligand interaction," *J. Am. Chem. Soc.* 117:174–1377.*
Arnon and Van Regenmortel, 1992, "Structural Basis of Antigenic Specificity and Design of New Vaccines," *FASEB J.* 6:3265–3274.*
Bai et al., 1993, "Primary Structure Effects on Peptide Group Hydrogen Exchange," *PROTEINS: Structure, Function, and Genetics* 17:75–86.*
Beasty and Matthews, 1985, "Characterization of an Early Intermediate in the Folding of the α–Subunit of Tryptophan Synthase by Hydrogen Exchange Measurement," *Biochemistry* 24:3547–3553.*
Benjamin et al., 1992, "Long–Range Changes in a Protein Antigen Due to Antigen–Antibody Interaction," *Biochemistry* 31:9539–9545.*
Breddam, 1986, "Serine Carboxypeptidases. A Review.," *Carlsberg Res. Commun.* 51:83–128.*
Burns et al., 1991, "Selective Reduction of Disulfides by Tris(2–Carboxyethyl)Phosphine," *J. Org. Chem.* 56:2648–2650.*
Burz and Allewell, 1986, "Mapping Structural Perturbations in *Escherichia coli* Aspartate Transcarbamylase by Medium Resolution Hydrogen Exchange," *Biophys J.* 49:70–72.
Byrne and Bryan, 1970, "An Improved Freeze–Drying Technique for the Study of Hydrogen Exchange of Proteins and Polypeptides," *Analytical Biochemistry* 33:414–428.
Carrey, "Peptide mapping," In: *Protein Structure: A Practical Approach*, Creighton, ed. IRL Press at Oxford University Press (1989) p. 117–144.
Chi and Baker, 1993, "Use of Deuterium–Hydrogen Exchange to Characterize the Fragmentation Pathways of Arteether and its Metabolites in a Thermospray Mass Spectrometer," *Organic Mass Spectrometry* 28:12–17.
Connelly et al., 1993, "Isotope Effects in Peptide Group Hydrogen Exchange," *PROTEINS: Structure, Function, and Genetics* 17:87–92.
Englander et al., 1969, "Hydrogen–Tritium Exchange of the Random Chain Polypeptide," *Biopolymers* 7:379–393.
Englander and Englander, 1972, "Hydrogen–Tritium Exchange," *Methods in Enzymology* 26:406–413.

(List continued on next page.)

*Primary Examiner*—Bennett Celsa
(74) *Attorney, Agent, or Firm*—Morgan, Lewis & Bockius, LLP

(57) ABSTRACT

The present invention provides methods whereby the positions of peptide amide groups that are labeled with a heavy hydrogen in a polypeptide or protein can be localized at high resolution. The methods are useful for determining which peptide amide groups in a polypeptide or protein are accessible to solvent, mapping the binding site and/or binding surface of a binding protein, and/or studying allosteric or other conformational changes in a polypeptide or protein which alter the rates at which certain peptide amide hydrogens exchange with solvent.

26 Claims, 13 Drawing Sheets

OTHER PUBLICATIONS

Englander and Rolfe, 1973, "Hydrogen Exchange Studies of Respiratory Proteins," *J. Biol. Chem.* 248(13):4852–4861.

Englander and Englander, 1978, "Hydrogen–Tritium Exchange," *Methods in Enzymology* 49:24–39.

Englander et al., 1979, "Individual Breathing Reactions Measured in Hemoglobin by Hydrogen Exchange Methods," *Biophys. J.* 10:577–589.

Englander and Englander, 1983, "Functional Labelling in Hemoglobin," *In: Structure and Dynamics: Nucleic Acids and Proteins*, Clementi and Sarma, eds. Adenine Press, NY, pp. 421–433.

Englander et al., 1983, "Identification of an Allosterically Sensitive Unfolding Unit in Hemoglobin," *J. Mol. Biol.* 169:325–344.

Englander et al., 1985, "Protein Hydrogen Exchange Studied by the Fragment Separation Method," *Analytical Biochemistry* 147:234–244.

Englander and Englander, 1987, "Hydrogen–Tritium Exchange Survey of Allosteric Effects in Hemoglobin," *Biochemistry* 26:1846–1850.

Englander et al., "The assignment of proton resonances in 2d NMR spectra of proteins," *Techniques in Protein Chemistry*, Hugli, T. E., ed. Academic Press, San Diego, pp. 207–222, 1989.

Fesik et al., 1987, "Amide Proton Exchange Rates of a Bound Pepsin Inhibitor Determined by Isotope–Edited Proton NMR Experiments," *Biochem. Biophys. Res. Commun.* 147(3):892–898.

Fusek et al., 1990, "Enzymic Properties of Thermopsin," *J. Biol. Chem.* 265(3):1496–1501.

Gray, 1993, "Disulfide Structures of Highly Bridged Peptides: A New Strategy for Analysis," *Protein Science* 2:1732–1748.

Gray, 1993, "Echistatin Disulfide Bridges: Selective Reduction and LInkage Assignment," *Protein Science* 2:1749–1755.

Hartman and Lee, 1989, "Examination of the Function of the Active Site Lysine 329 of Ribulose–Bisphosphate Carboxylase/Oxygenase as Revealed by the Proton Exchange Reaction," *J. Biol. Chem.* 246(20):11784–11789.

Hommel et al., 1991, "Structure–Function Relationships in Human Epidermal Growth Factor Studied by Site–Directed Mutagenesis and $^1$H NMR," *Biochemistry* 30:8891–8898.

Horsfall et al., 1991, "Epitope Mapping," *Immunology Today* 12(7):211–213.

Katta and Chait, 1993, "Hydrogen/Deuterium Exchange Electrospray Ionization Mass Spectrometry: A Method for Probing Protein Conformational Changes in Solution," *J. Am. Chem. Soc.* 115:6317–6321.

Kiefer et al., 1990, "Negative Screening for Sickle Cell Diseases with a Monoclonal Immunoassay on Newborn Blood Eluted from Filter Paper," *J. Lab. Clin. Med.* 116:826–830.

Kim and Baldwin, 1982, "Influence of Charge on the Rate of Amide Proton Exchange," *Biochemistry* 21(1):1–5.

Kirley, 1989, "Reduction and Fluorescent Labeling of Cyst(e)ine–Containing Proteins for Subsequent Structural Analyses," *Analytical Biochemistry* 180:231–236.

Krishnan and Vijayalakshmi, 1985, "Purification of an Acid Protease and a Serine Carboxypeptidase from *Aspergillus niger* Using Metal–Chelate Affinity Chromatography," *Journal of Chromatography* 329:165–170.

Levison et al., 1969, "Reduction of Biological Substances by Water–Soluble Phosphines: Gamma Globulin (IgG)," *Experientia* 25:126–127.

Loo et al., 1990, "Primary Sequence Information from Intact Proteins by Electrospary Ionization Tandem Mass Spectrometry," *Science* 248:201–204.

Louie et al., 1988, "Allosteric Energy at the Hemoglobin Beta Chain C Terminus Studies by Hydrogen Exchange," *J. Mol. Biol.* 201:755–764.

Louie et al., 1988, "Salt, Phosphate and the Bohr Effect at the Hemoglobin Beta Chain C Terminus Studied by Hydrogen Exchange," *J. Mol. Biol.* 201:765–772.

Mallikarachchi et al., 1989, "Effects of ATP and CTP on the Conformation of the Regulatory Subunit of *Escherichia coli* Aspartate Transcarbamylase in Solution: A Medium–Resolution Hydrogen Exchange Study," *Biochemistry* 28:5386–5391.

Matthyssens et al., 1972, "Study of the Thermal–Denaturation Mechanism of Hen Egg–White Lysozyme through Proteolytic Degradation," *Eur. J. Biochem.* 26:449–454.

Mayne et al., 1992, "Effect of Antibody Binding on Protein Motions Studies by Hydrogen–Exchange Labeling and Two–Dimensional NMR," *Biochemistry* 31:19678–10685.

McCloskey, 1990, "Introduction of Deuterium by Exchange for Measurement by Mass Spectrometry," *Methods in Enzymology* 193:329–338.

McCormick and Atassi, 1990, "Hemaglobin Binding with Haptoglobin: Delineation of the Haptoglobin Binding Site on the α–chain of Human Hemoglobin," *Journal of Protein Chemistry* 9(6):735–642.

Milne et al., 1998, "Determinants of protein hydrogen exchange studies in equine cytochrome c," *Protein Science* 7:739–745.

Molday et al., 1972, "Primary Structure Effects on Peptide Group Hydrogen Exchange," *Biochemistry* 11(2):150–158.

Mylvaganam et al., 1998, "Structural Basis for the Binding of an Anti–cytochrome c Antibody to its Antigen: Crystal Structures of FabE8–Cytochrome c Complex to 1.8 Å Resolution and FabE8 to 2.26 Å Resolution," *J. Mol. Biol.* 281:301–322.

Peterson et al., 1990, "An Antibody Binding Site on Cytochrome c Defined by Hydrogen Exchange and Two–Dimensionoal NMR," *Science* 249:755–759.

Ray and Englander, 1986, "Allosteric Sensitivity in Hemoglobin at the α–Subunit N–Terminus Studied by Hydrogen Exchange," *Biochemistry* 25:3000–3007.

Rogero et al., 1986, "Individual Breathing Reactions Measured by Functional Labeling and Hydrogen Exchange Methods," *Methods in Enzymology* 131:508–517.

Rosa and Richards, 1979, "An Experimental Procedure for Increasing the Structural Resolution of Chemistry Hydrogen–exchange Measurements on Proteins: Application to Ribonuclease S Peptide," *J. Mol. Biol.* 133:399–416.

Rosa and Richards, 1981, "Hydrogen Exchange from Identified Regions of the S–Protein Component of Ribonuclease as a Function of Temperature, pH, and Binding of S–Peptide," *J. Mol. Biol.* 145:835–851.

Rosa and Richards, 1982, "Effects of Binding of S–Peptide and 2'–Cytidine Monophosphate on Hydrogen Exchane from the S–Protein Component of Ribonuclease S," *J. Mol. Biol.* 160:517–530.

Rosnack and Stroh, 1992, "C–Terminal Sequencing of Peptides Using Electrospray Ionization Mass Spectrometry," *Rapid Communications in Mass Spectrometry* 6:637–640.

Reugg and Rudinger, 1977, "Reductive Cleavage of Cystine Disulfides with Tributylphoshpine," *Meth. Enzymol.* 47:111–117.

Schreier and Baldwin, 1976, "Concentration–Dependent Hydrogen Exchange Kinetics of $^3$H–Labeled S–Peptide in Ribonuclease S," *J. Mol. Biol.* 105:409–426.

Sepetov et al., 1993, "The Use of Hydrogen–Deuterium Exchange to Facilitate Peptide Sequencing by Electrospray Tandem Mass Spectrometry," *Rapid Communications in Mass Spectrometry* 7:58–62.

Smith and Duffin, 1993, "Carboxy–Terminal Protein Sequence Analysis Using Carboxypeptidase P and Electrospray Mass Spectrometry," *Techniques in Protein Chemistry IV* 463–470.

Takahashi and Tang, 1981, "Cathepsin D From Porcine and Bovine Spleen," *Methods in Enzymology* 80:565–581.

Thevenon–Emeric et al., 1992, "Determination of Amide Hydrogen Exchange Rates in Peptides by Mass Spectrometry," *Anal. Chem.* 64:2456–2458.

Tsugita et al., 1982, "Exopeptidase digestion in combination with field desorption mass spectroscopy for amino acid sequence determination," *FEBS Letters.* 137(1): 19–24.

Tsugita, 1987, "Developments in Protein Microsequencing," *Adv. Biophys.* 23:81–113.

Tsugita et al., 1993, "Development of Novel C–Terminal Sequencing Methods," *Methods in Protein Sequence Analysis*, edited by K. Imahori, F. Sakiyama, Plenum Press, New York, pp. 55–62.

Tsugita et al., 1992, "Reaction of Pentafluoropropionic Anhydride Vapor on Polypeptide as Revealed by Mass Spectrometry. A Carboxypeptidase Mimetic Degradation," *Chemistry Letters*: 235–238.

Wang et al., 1997, "Hydrogen exchange/electrospray ionization mass spectrometry studies of substrate and inhibitor binding and conformation changes of *Escherichia coli* dihydrodipicolinate reductase," *Biochemistrty* 36(13):3755–3759.

Winger et al., 1992, "Probing Qualitative Conformation Differences of Multiply Protonated Gas–Phase Proteins via H/D Isotopic Exchange with $D_2O$," *J. Am. Chem. Soc.* 114:5897–5898.

Xiaoming and Breddam, 1989, "A Novel Carboxylesterase from *Aspergillus niger* and its Hydrolysis of Succinimide Esters," *Carlsberg Res. Commun.* 54:241–249.

Yoshioka and Atassi, 1986, "Haemoglobin Binding with Haptoglobin," *Biochem. J.* 234:453–456.

Zhang and Smith, 1993, "Determination of Amide Hydrogen Exchange by Mass Spectrometry: A New Tool for Protein Structure Elucidation," *Protein Science* 2:522–531.

Zhang et al., 1995, "Rapid amide proton exchange rates in peptides and proteins measured by solvent quenching and two–dimensional NMR," *Protein Science* 4:804–814.

Zhu et al., 1990, "Purification and Characterization of an Extracellular Acid Proteinase from the Ectomycorrhizal Fungus, *Hebeloma crustuliniforme*," *Applied and Environmental Microbiology* 56:837–843.

\* cited by examiner

UNREDUCED ENDOTHELIN=48%

UNREDUCED ENDOTHELIN=48%

UNREDUCED ENDOTHELIN=44%

UNREDUCED ENDOTHELIN=44%

METHODS FOR THE HIGH-RESOLUTION IDENTIFICATION OF SOLVENT-ACCESSIBLE AMIDE HYDROGENS IN PROTEIN BINDING SITES

This application is a divisional of application Ser. No. 08/919,187, filed Aug. 19, 1997, now U.S. Pat. No. 6,291,189, which is a continuation-in-part of application Ser. No. 08/895,330, entitled "Methods for Characterization of the Fine Structure of Protein Binding Sites", filed Jul. 16, 1997, now U.S. Pat. No. 6,331,400, which is a continuation of application Ser. No. 08/240,593, filed May 10, 1994 now U.S. Pat. No. 5,658,739, each of which is hereby incorporated herein in its entirety by reference.

BACKGROUND OF THE INVENTION

1. Field of the Invention

The present invention relates to the identification of solvent-accessible amide hydrogens in polypeptides or proteins. The methods of the invention can be used to characterize the binding site involved in binding between a binding protein and a binding partner, and to study other changes in a polypeptide or protein which alter the rates at which hydrogen atoms exchange with solvent hydrogens, such as folding phenomena and other structural changes.

2. Background Art

Limitations of Current Methods of Characterizing Protein Binding Sites

Considerable experimental work and time are required to precisely characterize a binding site. In general, the techniques which are the easiest to use and which give the quickest answers, result in an inexact and only approximate idea of the nature of the critical structural features. Techniques in this category include the study of proteolytically generated fragments of the protein which retain binding function; recombinant DNA techniques, in which proteins are constructed with altered amino acid sequence (site directed mutagenesis); epitope scanning peptide studies (construction of a large number of small peptides representing subregions of the intact protein followed by study of the ability of the peptides to inhibit binding of the ligand to receptor); covalent crosslinking of the protein to its binding partner in the area of the binding site, followed by fragmentation of the protein and identification of crosslinked fragments; and affinity labeling of regions of the receptor which are located near the ligand binding site of the receptor, followed by characterization of such "nearest neighbor" peptides. (Reviewed in 1, 2).

These techniques work best for the determination of the structure of binding subregions which are simple in nature, as when a single short contiguous stretch of polypeptide within a protein is responsible for most of the binding activity. However, for many protein-binding partner systems of current interest, the structures responsible for binding on both receptor and ligand or antibody are created by the complex interaction of multiple non-contiguous peptide sequences. The complexities of these interactions may confound conventional analytical techniques, as binding function is often lost as soon as one of the 3-dimensional conformations of the several contributing polypeptide sequences is directly or indirectly perturbed.

The most definitive techniques for the characterization of the structure of receptor binding sites have been NMR spectroscopy and X-ray crystallography. While these techniques can ideally provide a precise characterization of the relevant structural features, they have major limitations, including inordinate amounts of time required for study, inability to study large proteins, and, for X-ray analysis, the need for protein-binding partner crystals (Ref. 3).

Applicant's technology overcomes these limitations and allows the rapid identification of each of the specific polypeptides and amino acids within a protein which constitute its protein ligand binding site or antibody binding subregion in virtually any protein-ligand system or protein antigen-antibody system, regardless of the complexity of the binding sites present or the size of the proteins involved. This technology is superior in speed and resolution to currently employed biochemical techniques.

Hydrogen (Proton) Exchange

When a protein in its native folded state is incubated in buffers containing heavy hydrogen (tritium or deuterium) labeled water, heavy hydrogen in the buffer reversibly exchanges with normal hydrogen present in the protein at acidic positions (for example, O—H, S—H, and N—H groups) with rates of exchange which are dependent on each exchangeable hydrogen's chemical environment, temperature, and most importantly, its accessibility to the tritiated water in the buffer. (Refs. 4, 5) Accessibility is determined in turn by both the surface (solvent-exposed) disposition of the hydrogen, and the degree to which it is hydrogen-bonded to other regions of the folded protein. Simply stated, acidic hydrogen present on amino acid residues which are on the outside (buffer-exposed) surface of the protein and which are hydrogen-bonded to solvent water will exchange more rapidly with heavy hydrogen in the buffer than will similar acidic hydrogen which are buried and hydrogen bonded within the folded protein.

Hydrogen exchange reactions can be greatly accelerated by both acid and base-mediated catalysis, and the rate of exchange observed at any particular pH is the sum of both acid and base mediated mechanisms. For many acidic hydrogen, a pH of 2.7 results in an overall minimum rate of exchange (Ref. 6, pg. 238, FIGS. 3a–c, refs. 7–11). While hydrogens in protein hydroxyl and amino groups exchange with tritium in buffer at millisecond rates, the exchange rate of one particular acidic hydrogen, the peptide amide bond hydrogen, is considerably slower, having a half life of exchange (when freely hydrogen bonded to solvent water) of approximately 0.5 seconds at 0° C., pH 7, which is greatly slowed to a half life of exchange of 70 minutes at 0° C. pH 2.7.

When peptide amide hydrogens are buried within a folded protein, or are hydrogen bonded to other parts of the protein, exchange half lives with solvent hydrogens are often considerably lengthened, at times being measured in hours to days. Hydrogen exchange at peptide amides is a fully reversible reaction, and rates of on-exchange (solvent heavy hydrogen replacing protein-bound normal hydrogen) are identical to rates of off-exchange (hydrogen replacing protein-bound heavy hydrogen) if the state of a particular peptide amide within a protein, including its chemical environment and accessibility to solvent hydrogens, remains identical during on-exchange and off-exchange conditions.

Hydrogen exchange is commonly measured by performing studies with proteins and aqueous buffers that are differentially tagged with pairs of the three isotopic forms of hydrogen ($^1$H;Normal Hydrogen; $^2$H;Deuterium; $^3$H;Tritium). If the pair of normal hydrogen and tritium are employed, it is referred to as tritium exchange; if normal hydrogen and deuterium are employed, as deuterium exchange. Different physicochemical techniques are in general used to follow the distribution of the two isotopes in deuterium versus tritium exchange.

Tritium Exchange Techniques

Tritium exchange techniques (where the amount of the isotope is determined by radioactivity measurements) have been extensively used for the measurement of peptide amide exchange rates within an individual protein (reviewed in 4). The rates of exchange of other acidic protons (OH, NH, SH) are so rapid that they cannot be followed in these techniques and all subsequent discussion refers exclusively to peptide amide proton exchange. In these studies, purified proteins are on-exchanged by incubation in buffers containing tritiated water for varying periods of time, transferred to buffers free of tritium, and the rate of off-exchange of tritium determined. By analysis of the rates of tritium on- and off-exchange, estimates of the numbers of peptide amide protons in the protein whose exchange rates fall within particular exchange rate ranges can be made. These studies do not allow a determination of the identity (location within the protein's primary amino acid sequence) of the exchanging amide hydrogens measured.

Extensions of these techniques have been used to detect the presence within proteins of peptide amides which experience allosterically-induced changes in their local chemical environment and to study pathways of protein folding (5, 12–14). For these studies, tritium on-exchanged proteins are allowed to off-exchange after they have experienced either an allosteric change in shape, or have undergone time-dependent folding upon themselves, and the number of peptide amides which experience a change in their exchange rate subsequent to the allosteric/folding modifications determined. Changes in exchange rate indicate that alterations of the chemical environment of particular peptide amides have occurred which are relevant to proton exchange (solvent accessibility, hydrogen bonding etc.). Peptide amides which undergo an induced slowing in their exchange rate are referred to as "slowed amides" and if previously on-exchanged tritium is sufficiently slowed in its off-exchange from such amides there results a "functional tritium labeling" of these amides. From these measurements, inferences are made as to the structural nature of the shape changes which occurred within the isolated protein. Again, determination of the identity of the particular peptide amides experiencing changes in their environment is not possible with these techniques.

Four groups of investigators have described technical extensions (collectively referred to as medium resolution tritium exchange) which allow the locations of particular slowed, tritium labeled peptide amides within the primary sequence of small proteins to be localized to a particular proteolytic fragment, though not to a particular amino acid.

Rosa and Richards were the first to describe and utilize medium resolution tritium techniques in their studies of the folding of ribonuclease S protein fragments (15–17). However, the techniques described by Rosa and Richards were of marginal utility, primarily due to their failure to optimize certain critical experimental steps (reviewed in 6, pg 238, 244). No studies employing related techniques were published until the work of Englander and co-workers in which extensive modifications and optimizations of the Rosa and Richards technique were first described.

Englander's investigations utilizing tritium exchange have focused exclusively on the study of allosteric changes which take place in tetrameric hemoglobin (a subunit and b subunit 16 kD in size each) upon deoxygenation (6,18–21). In the Englander procedure, native hemoglobin (milligram quantities) in the oxygenated state is on-exchanged in tritiated water of relatively low specific activity (2–100 mCi/ml). The hemoglobin is then deoxygenated (inducing allosteric change), transferred to tritium-free buffers by gel permeation column chromatography, and then allowed to out-exchange for 10–50 times the on-exchange time. On-exchanged tritium present on peptide amides which experience no change in exchange rate subsequent to the induced allosteric change in hemoglobin structure off-exchanges at rates identical to its on-exchange rates, and therefore is almost totally removed from the protein after the long off-exchange period. However, peptide amides which experience slowing of their exchange rate subsequent to the induced allosteric changes preferentially retain the tritium label during the period of off-exchange.

To localize (in terms of hemoglobin's primary sequence) the slowed amides bearing the residual tritium label, Englander then proteolytically fragments the off-exchanged hemoglobin with the protease pepsin, separates, isolates and identifies the various peptide fragments by reverse phase high pressure liquid chromatography (RP-HPLC), and determines which fragments bear the residual tritium label by scintillation counting. However, as the fragmentation of hemoglobin proceeds, each fragment's secondary and tertiary structure is lost and the unfolded peptide amides become freely accessible to $H_2O$ in the buffer. At physiologic pH (>6), any amide-bound tritium label would leave the unfolded fragments within seconds. Englander therefore performs the fragmentation and HPLC peptide isolation procedures under conditions which he believes minimize peptide amide proton exchange, including cold temperature (4° C.) and use of phosphate buffers at pH 2.7 (reviewed in 6). This technique has been used successfully by Englander to coarsely identify and localize the peptidic regions of hemoglobin α and β chains which participate in deoxygenation-induced allosteric changes (18–21). The ability of the Englander technique to localize tritium labeled amides, while an important advance, remains low; at the best, Englander reports that his technique localizes amide tritium label to hemoglobin peptides 14 amino acids or greater in size, without the ability to further sublocalize the label.

Moreover, in Englander's work, there is no appreciation that a suitably adapted tritium exchange technique might be used to identify the peptide amides which reside in the contacting surface of a protein receptor and its binding partner: his disclosures are concerned exclusively with the mapping of allosteric changes in hemoglobin. Furthermore, based on his optimization studies (6–11,13), Englander teaches and warns that a pH of 2.7 must be employed in both the proteolysis and HPLC steps, necessitating the use of proteases which are functional at these pH's (acid proteases). Unfortunately, acid proteases are relatively non-specific in their sites of proteolytic cleavage, leading to the production of a very large number of different peptide fragments and hence to considerable HPLC separation difficulties. The constraint of performing the HPLC separation step at pH 2.7 greatly limits the ability to optimize the chromatographic separation of multiple overlapping peptides by varying the pH at which HPLC is performed. Englander tried to work around these problems, for the localization of hemoglobin peptides experiencing allosteric changes, by taking advantage of the fact that some peptide bonds are somewhat more sensitive to pepsin than others. He therefore limits the duration of exposure of the protein to pepsin to reduce the number of fragments. Even then the fragments were "difficult to separate cleanly". They were also, of course, longer (on average), and therefore the resolution was lower. He also tried to simplify the patterns by first separating the alpha and beta chains of hemoglobin.

However, there was a tradeoff: increased tritium loss during the alpha-beta separation and the removal of the solvent, preparatory to proteolysis. Englander concludes, "At present the total analysis of the HX (hydrogen exchange) behavior of a given protein by these methods is an immense task. In a large sense, the best strategies for undertaking such a task remain to be formulated. Also, these efforts would benefit from further technical improvements, for example in HPLC separation capability and perhaps especially in the development of additional acid proteases with properties adapted to the needs of these experiments" (6).

Over the succeeding years since this observation was made, no advances have been disclosed which address these critical limitations of the medium resolution tritium exchange technique. It has been perceived that improvements to the HPLC separation step were problematic due to the constraint of working at pH 2.7. The current limited success with small proteins has made it pointless to attempt similar studies of larger proteins where the problems of inadequate HPLC peptide separation at pH 2.7, and imprecision in the ability to sublocalize labeled amides would be greatly compounded. Furthermore, most acid-reactive proteases are in general no more specific in their cleavage patterns than pepsin and efforts to improve the technology by employing other acid reactive proteases other than pepsin have not significantly improved the technique. Given these limitations of medium resolution tritium exchange art, no studies have been disclosed which utilize proteins with subunit size greater than 16 kilodaltons.

Allewell and co-workers have disclosed studies utilizing the Englander techniques to localize induced allosteric changes in the enzyme *Escherichia coli* aspartate transcarbamylase (22,23). Burz, et al. (22) is a brief disclosure in which the isolated R2 subunit of this enzyme is on-exchanged in tritiated buffer of specific activity 100 mCi/ml, allosteric change induced by the addition of ATP, and then the conformationally altered subunit off-exchanged. The enzyme R2 subunit was then proteolytically cleaved with pepsin and analyzed for the amount of label present in certain fragments. Analysis employed techniques which rigidly adhered to the recommendations of Englander, utilizing a single RP HPLC separation in a pH 2.8 buffer.

The authors note difficulty in separating the large number of peptides generated, even from this small protein subfragment, given the constraints of the Englander methodology. They comment that "the principal limitation of this method at present is the separation with columns now available". ATP binding to the enzyme was shown to alter the rate of exchange of hydrogens within several relatively large peptidic fragments of the R2 subunit. In a subsequent more complete disclosure (23), the Allewell group discloses studies of the allosteric changes induced in the R2 subunit by both ATP and CTP. They disclose on-exchange of the R2 subunit in tritiated water-containing buffer of specific activity 22–45 mCi/ml, addition of ATP or CTP followed by off exchange of the tritium in normal water-containing buffer. The analysis comprised digestion of the complex with pepsin, and separation of the peptide fragments by reverse phase HPLC in a pH 2.8 or pH 2.7 buffer, all of which rigidly adheres to the teachings of Englander. Peptides were identified by amino acid composition or by N-terminal analysis, and the radioactivity of each fragment was determined by scintillation counting. In both of these studies the localization of tritium label was limited to peptides which averaged 10–15 amino acids in size, without higher resolution being attempted.

Beasty, et al. (24) have disclosed studies employing tritium exchange techniques to study folding of the a subunit of *E. Coli* tryptophan synthetase. The authors employed tritiated water of specific activity 20 mCi/ml, and fragmented the tritium labeled enzyme protein with trypsin at a pH 5.5, conditions under which the protein and the large fragments generated retained sufficient folded structure as to protect amide hydrogens from off exchange during proteolysis and HPLC analysis. Under these conditions, the authors were able to produce only 3 protein fragments, the smallest being 70 amino acids in size. The authors made no further attempt to sublocalize the label by further digestion and/or HPLC analysis. Indeed, under the experimental conditions they employed (they performed all steps at 12° C. instead of 4° C., and performed proteolysis at pH 5.5 instead of pH in the range of 2–3), it would have been impossible to further sublocalize the labeled amides by tritium exchange, as label would have been immediately lost (off-exchanged) by the unfolding of subsequently generated proteolytic fragments at pH 5.5 if they were less than 10–30 amino acids in size.

Fromageot, et al., U.S. Pat. No. 3,828,102 (25) discloses using hydrogen exchange to tritium label a protein and its binding partner, and Benson, U.S. Pat. No. 3,560,158 and 3,623,840 (26) disclose using hydrogen exchange to tritiate compounds for analytical purposes.

However, none of the methods described in the art are capable of localizing the positions of the tritium labels of the labeled proteins at high resolution, the best resolution in the art generally being on the order of $\geq 14$ amino acid residues.

Deuterium Exchange Techniques

Fesik, et al (27) discloses measuring by NMR the hydrogen (deuterium) exchange of a peptide before and after it is bound to a protein. From this data, the interactions of various hydrogens in the peptide with the binding site of the protein are analyzed.

Patterson, et al. (28) and Mayne, et al. (29) disclose NMR mapping of an antibody binding site on a protein (cytochrome-C) using deuterium exchange. This relatively small protein, with a solved NMR structure, is first complexed to anti-cytochrome-C monoclonal antibody, and the preformed complex then incubated in deuterated water-containing buffers and NMR spectra obtained at several time intervals. The NMR spectra of the antigen-antibody complex is examined for the presence of peptide amides which experience slowed hydrogen exchange with solvent deuterium as compared to their rate of exchange in uncomplexed native cytochrome-C. Benjamin, et al. (30) employ an identical NMR-deuterium technique to study the interaction of hen egg lysozyme (HEL) with HEL-specific monoclonal antibodies. While both this NMR-deuterium technique, and medium resolution tritium exchange rely on the phenomenon of proton exchange at peptide amides, they utilize radically different methodologies to measure and localize the exchanging amides. Furthermore, study of proteins by the NMR technique is not possible unless the protein is small (less than 30 kD), large amounts of the protein are available for the study, and computationally intensive resonance assignment work is completed.

Recently, others (45–50) have disclosed techniques in which exchange-deuterated proteins are incubated with binding partner, off-exchanged, the complex fragmented with pepsin, and deuterium-bearing peptides identified by single stage fast atom bombardment (Fab) or electrospray mass spectroscopy (MS). In these studies, no attempt has been made to sublocalize peptide-bound deuterium within the proleolytically or otherwise generated peptide fragments.

Thus, as is evidenced by the above discussion, there remains a need in the art for simple and efficient methods whereby the positions of labeled solvent-accessible peptide amide hydrogens can be localized at high resolution within the primary amino acid sequence of a polypeptide or protein, as well as simple and efficient methods for studying or mapping the binding sites and/or interaction surfaces of a polypeptide or protein. Accordingly, these are objects of the present invention.

SUMMARY OF THE INVENTION

These and other shortcomings in the art are overcome by the present invention, which in one aspect provides methods for the functional labeling and identification of specific amino acid residues that participate in binding protein-binding partner interactions. The methods of the invention are particularly suitable for the study of the binding protein-binding partner subregions of large (>30 KD) proteins, even in small quantities.

In one embodiment, the label is tritium and the amount of label on a fragment or subfragment is determined by measuring its radioactivity. In a second embodiment, the label is deuterium and the amount of label on a fragment or subfragment is determined by mass spectrometry. The term "heavy hydrogen" is used herein to refer generically to either tritium or deuterium. In addition, references to tritium apply mutatis mutandis to deuterium except when clearly excluded.

In essence, the binding protein is first tritiated or deuterated under conditions wherein native hydrogens are replaced by the tritium or deuterium label (this is the "on-exchange" step). Then the binding partner is allowed to interact with labeled protein. The binding partner occludes the binding site and protects the tritium or deuterium labels of that site from a subsequent "off-exchange". Thus, after the "off-exchange", only the binding site residues are labeled. Since the binding site is normally only a small portion of the molecules, a higher signal-to-background ratio is obtained with this approach than with Englander's more conventional procedure.

In order to actually identify the labeled residues, one must first dissociate the complex under slow hydrogen isotope exchange ($H^3/H^1$ or $H^2/H^1$) conditions, since otherwise the labels would leave the binding site as soon as the ligand was removed. The binding protein is then optionally fragmented (e.g., with an endoprotease such as pepsin), still under slow hydrogen exchange conditions, to obtain fragments. Those fragments which bear label presumably include binding site residues. At this point, the resolution of the binding site is no better than the fragment size.

A finer localization of the labels is achieved by analysis of subfragments generated by controlled, stepwise, degradation of the binding protein or of each isolated, labeled peptide fragment (if the binding protein was optionally fragmented) under slowed exchange conditions. For the purpose of the present invention, the protein or a peptide fragment is said to be "progressively", "stepwise" or "sequentially" degraded if a series of fragments are obtained which are similar to those which would be achieved by an ideal exopeptidase. For an ideal exopeptidase, only an end amino acid is removed. Thus, if the n amino acids of a peptide were labeled $A_1$ to $A_n$ (the numbering starting at whichever end the degradation begins), the series of subfragments produced by an ideal exopeptidase would be $A_2 \ldots A_n, A_3 \ldots A_n, \ldots, A_{n-1}-A_n$, and finally An. However, it is to be understood that while preferably each subfragment of the series of subfragments obtained is shorter than the preceding subfragment in the series by a single terminal amino acid residue, exopeptidases are not necessarily ideal. Thus, for purposes of the present invention, a fragment is said to be "progressively," "stepwise" or "sequentially" degraded if a series of subfragments is generated wherein each subfragment in the series is composed of about 1–5 fewer terminal amino acid residues than the preceding subfragment in the series. The signals produced by the successive subfragments are correlated in order to determine which amino acids of the fragment in question were labeled.

This procedure was not used in any of the cited references to further localize the labeling sites, though improved resolution was certainly a goal of the art. The closest the art comes is Englander's general suggestions of further fragmentations with another "acid protease".

The progressive degradation is preferably achieved by an enzyme, and more preferably by a carboxypeptidase. The need to employ an acidic pH at the time of degradation to minimize tritium losses discourages use of carboxypeptidases which are substantially inactivated by the required acidic buffers. However, carboxypeptidase-P, carboxypeptidase Y, and several other acid-reactive (i.e., enzymatically active under acid conditions) carboxypeptidases are suitable for proteolysis of peptides under acidic conditions, even at pH 2.7.

Progressive subfragmentation of purified tritium label-bearing peptides is performed with acid-reactive carboxypeptidases under conditions that produce a complete set of amide-labeled daughter peptides each shorter than the preceding one by 1–5 carboxy terminal amino acids, and preferably by a single carboxy-terminal amino acid. HPLC analysis of the several members of this set of progressively truncated peptides allows the reliable assignment of label to a particular amide position within the parent peptide.

Alternatively, the present invention contemplates C-terminal chemical degradation techniques that can be performed under "slow hydrogen exchange conditions" e.g., by pentafluoropropionic acid anhydride. The sensitivity of the technique may be improved by the use of reference peptide subfragments as HPLC mobility markers.

In general, the art has given insufficient consideration to the problems of denaturing the binding protein sufficiently to facilitate proteolysis under slow hydrogen exchange conditions. Pepsin, for example, is much less active at 0° C. than at room temperature. While pepsin is able to extensively digest hemoglobin that has been denatured by acidic pH at 0° C., certain other binding proteins, such as hen egg lysozyme, are much more resistant to denaturation by slow H-exchange conditions, and hence to subsequent pepsin digestion. As a result, many fewer and longer fragments are generated. This complicates the analysis.

In a preferred embodiment, the labeled binding protein is exposed, before fragmentation, to denaturing conditions compatible with slow hydrogen exchange and sufficiently strong to denature the protein enough to render it adequately susceptible to the intended proteolytic treatment. If these denaturing conditions would also denature the protease, then, prior to proteolysis, the denatured protein is switched to less denatured conditions (still compatible with slow H-exchange) sufficiently denaturing to maintain the protein in a protease-susceptible state but substantially less harmful to the protease in question.

Preferably, the initial denaturant is guanidine thiocyanate, and the less denaturing condition is obtained by dilution with guanidine HCl.

Disulfide bonds, if present in the binding protein to be digested, can also interfere with analysis. Disulfide bonds can hold the protein in a folded state where only a relatively small number of peptide bonds are exposed to proteolytic attack. Even if some peptide bonds are cleaved, failing to disrupt the disulfide bonds would reduce resolution of the peptide fragments still joined to each other by the disulfide bond; instead of being separated, they would remain together. This would reduce the resolution by at least a factor of two (possibly more, depending on the relationship of disulfide bond topology to peptide cleavage sites). If the disulfide bonds are not disrupted, further sublocalization of the tritium-labeled amides within each of the disulfide-joined peptides would be very difficult, as amino acid removal would occur, at different times and at different rates, at each C-terminal of the disulfide linked segments.

The applicant has discovered that water soluble phosphines may be used to disrupt a protein's disulfide bonds under "slow hydrogen exchange" conditions. This allows much more effective fragmentation of large proteins which contain disulfide bonds without causing tritium label to be lost from the protein or its proteolytic fragments (as would be the case with conventional disulfide reduction techniques which must be performed at pH's which are very unfavorable for preservation of tritium label).

In another embodiment, peptide amides on the binding protein's surface are indirectly labeled by transfer of tritium or deuterium that has been previously attached by hydrogen exchange to the interaction surface of the binding partner. This procedure will functionally label receptor protein amides if they are slowed by complex formation and are also in intimate contact with the binding partner, in the complexed state. Amides that are distant from the interaction surface but slowed in exchange because of complex formation-induced allosteric changes in the protein will not be labeled.

In another aspect, the present invention provides a method for determining which peptide amide hydrogens in a polypeptide or protein are accessible to solvent. By using the method of the invention, the positions of solvent-accessible peptide amide hydrogens within a polypeptide or protein can be localized at high resolution, i.e., typically within 5 or fewer amino acid residues, and in many instances to within a single amino acid residue.

In the method, solvent accessible peptide amide hydrogens of a polypeptide or protein of interest are on-exchanged by contacting the polypeptide or protein with heavy hydrogen under conditions wherein the native solvent-accessible peptide amide hydrogens are replaced with heavy hydrogen (deuterium or tritium), such as, for example, physiological conditions wherein the polypeptide or protein is folded into its native conformation. Peptide amide protons that are inaccessible to solvent, such as those that are buried within the interior of the polypeptide or protein structure or those that participate in intramolecular hydrogen-bonding interactions, do not readily exchange with the heavy hydrogens in the solvent. Thus, those peptide amide hydrogens that are solvent-accessible are selectively labeled with heavy hydrogen.

The positions of the labeled peptide amide hydrogens within the polypeptide or protein can be localized at high resolution by progressively generating a series of subfragments under conditions of slowed exchange as previously described, determining which subfragments are labeled and correlating the sequences of the labeled subfragments with the sequence of the polypeptide or protein to determine which peptide amide groups in the polypeptide or protein were labeled, and thus accessible to solvent.

In some embodiments, especially those wherein the polypeptide or protein of interest is relatively large, the polypeptide or protein may optionally be first fragmented (e.g., with an endoprotease or mixture of endoproteases) under conditions of slowed exchange as previously described, and the positions of the labels localized to high resolution by progressively degrading each labeled fragment into a series of subfragments, determining which subfragments are labeled and correlating the sequences of the labeled subfragments to the sequences of the labeled fragments and, ultimately, to the sequence of the polypeptide or protein, as previously described.

In a preferred embodiment, the polypeptide or protein is denatured and any disulfide bonds reduced under conditions of slowed exchange prior to fragmentation and/or subfragmentation.

BRIEF DESCRIPTION OF THE DRAWINGS

FIG. 1a: Absorbance (214 nm) tracing of unlabeled proteolyzed Hgb. FIG. 1b: Hgb on-exchanged for 4 hours, shifted to pH 2.7 and then proteolyzed without off exchange. FIG. 1c: Hgb on-exchanged for 4 hours, mixed with monoclonal antibody β6 and then off-exchanged for 40 hours before proteolysis at pH 2.7. FIG. 1d: Hgb on-exchanged for 4 hours and then off-exchanged for 40 hours before proteolysis at pH 2.7.

FIG. 3a: Hgb on-exchanged for 4 hours then proteolyzed without a period of off exchange. FIG. 3b: Hgb on-exchanged for 4 hours, mixed with monoclonal antibody β121 and then off-exchanged for 40 hours. FIG. 3c: Hgb on-exchanged for 4 hours and then off-exchanged for 40 hours.

FIG. 4a: HPLC optical density tracing. FIG. 4b: Hgb on-exchanged for 4 hours then proteolyzed without a period of off exchange. FIG. 4c: Hgb on-exchanged for 4 hours, mixed with haptoglobin and then off-exchanged for 40 hours. FIG. 4d: Hgb on-exchanged for 4 hours and then off-exchanged for 40 hours.

FIG. 5A: β6 monoclonal interaction peptides; FIG. 5B: β121 monoclonal interaction peptides.

FIGS. 6a, 6b—no digestion; FIGS. 6c, 6d—2.5 min. digestion with 0.1 mg/ml carboxypeptidase-P; FIGS. 6e, 6f—2.5 min. digestion with 0.5 mg/ml carboxypeptidase-P; FIGS. 6g, 6h—5 min. digestion with 1.0 mg/ml carboxypeptidase-P; and FIGS. 6i, 6j—15 min. digestion with 1.0 mg/ml carboxypeptidase-P;. HPLC analysis was then performed as in FIGS. 1a–d, but with simultaneous measurement of O.D.214 nm and radioactivity of column effluent. The positions of the several generated C-terminal truncated peptide fragments are indicated (numbers 3 through 9). Progressive generation of fragments is observed.

(FIGS. 7a, 7b (5 mins.); FIGS. 7e, 7f (5 mins.); FIGS. 7g, 7h (10 mins.); FIGS. 7i, 7j (30 mins.)), 2 minutes at 22° C. (FIGS. 7c, 7d). The mixtures were then subjected to HPLC as in FIGS. FIGS. 6a–j. The percent of endothelin that remained unreduced under each condition is indicated. The fraction of tritium label that remained attached to the β1–14 peptide is: FIG. 7b (0.35); FIG. 7d (0.25); FIG. 7f (0.38); FIG. 7h (0.35); FIG. 7j (0.32). Fifty percent reduction of endothelium disulfides is accomplished at pH 2.7 with an insignificant loss of peptide amide-bound tritium from the β1–14 peptide. "R" indicates the positions of reduced forms of endothelin.

DETAILED DESCRIPTION OF THE PREFERRED EMBODIMENTS

Biochemical Binding, Generally

Figure 1A:
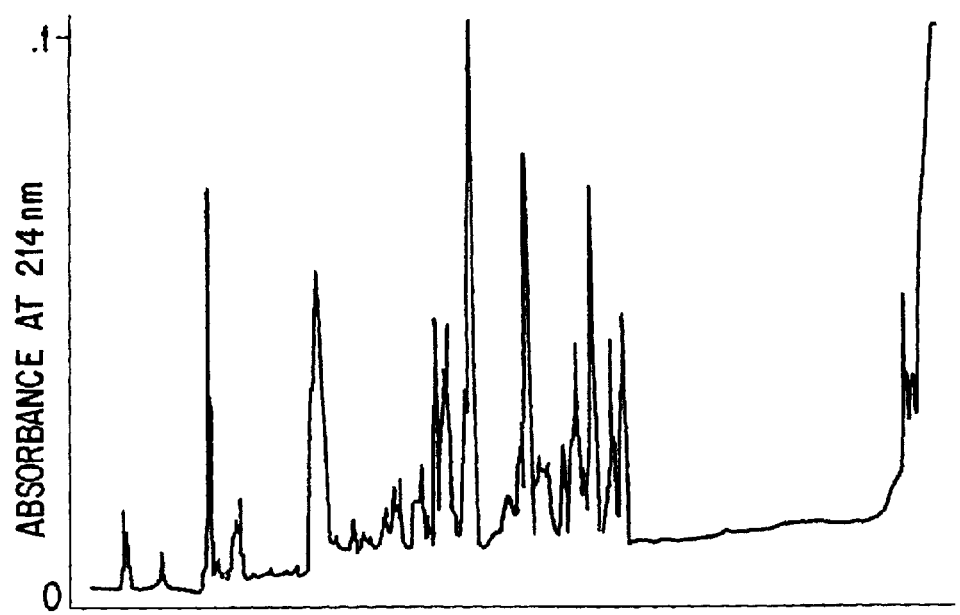
FIGS. 1a–1d depict the results of analysis of tritium associated with hemoglobin (Hgb) fragments produced by pepsin digestion of tritium-exchanged hemoglobin±monoclonal, antibody followed by HPLC in $PO_4$ buffered solvents, pH 2.7.

Many biological processes are mediated by noncovalent binding interactions between a protein and another molecule, its binding partner. The identification of the structural features of the two binding molecules which immediately contribute to those interactions would be useful in designing drugs which alter these processes.

The molecules which preferentially bind each other may be referred to as members of a "specific binding pair". Such pairs include an antibody and its antigen, a lectin and a carbohydrate which it binds, an enzyme and its substrate, and a hormone and its cellular receptor. In some texts, the terms "receptor" and "ligand" are used to identify a pair of binding molecules. Usually, the term "receptor" is assigned to a member of a specific binding pair which is of a class of molecules known for its binding activity, e.g., antibodies. The term "receptor" is also preferentially conferred on the member of the pair which is larger in size, e.g., on avidin in the case of the avidin-biotin pair. However, the identification of receptor and ligand is ultimately arbitrary, and the term "ligand" may be used to refer to a molecule which others would call a "receptor". The term "anti-ligand" is sometimes used in place of "receptor".

While binding interactions may occur between any pair of molecules, e.g., two strands of DNA, the present specification is primarily concerned with interactions in which at least one of the molecules is a protein. Hence, it is convenient to speak of a "binding protein" and its "binding partner". The term "protein" is used herein in a broad sense which includes, mutatis mutandis, polypeptides and oligopeptides, and derivatives thereof, such as glycoproteins, lipoproteins, and phosphoproteins, and metalbproteins. The essential requirement is that the "binding protein" feature one or more peptide (—NHCO—) bonds, as the amide hydrogen of the peptide bond (as well as in the side chains of certain amino acids) has certain properties which lends itself to analysis by proton exchange.

The binding protein may be identical to a naturally occurring protein, or it may be a binding fragment or other mutant of such a protein. The fragment or mutant may have the same or different binding characteristic relative to the parental protein.

Integral membrane proteins are of particular interest, as they are difficult to crystallize for study by X-ray diffraction. Proteins too large to study by NMR methods, e.g., those larger than about 50 kDa, are also of special interest, particularly if they cannot be characterized as a composite of two or more separately analyzable domains. Examples of suitable proteins include integrins (which are large integral membrane proteins), cell surface receptors for growth factors (including cytokine receptors), "seven-spanners", selectin, and cell surface receptors of the immunoglobin superfamily (e.g., ICAM-1).

The method of the present invention is especially useful for studying proteins with discontinuous epitopes, such as certain antibodies, including certain clinically important autoimmune antibodies.

A "binding site" is a point of contact between a binding surface ("paratope") of the binding protein and a complementary surface ("epitope") of the binding partner. (When the binding partner is a protein, the designation of "paratope" and "epitope" is essentially arbitrary. However, in the case of antibody-antigen interactions, it is conventional to refer to the antigen binding site of the antibody as the "paratope" and the target site on the antigen as the "epitope".) A specific binding pair may have more than one binding site, and the term "pair" is used loosely, as the binding protein may bind two or more binding partners (as in the case of a divalent antibody). Moreover, other molecules, e.g., allosteric effectors, may alter the conformation of a member of the "pair" and thereby modulate the binding. The term "pair" is intended to encompass these more complex interactions.

Slowed Hydrogen Exchange Conditions

The present invention contemplates labeling the binding site of a binding protein (or binding partner) with a heavy hydrogen isotope, and determining the location of the labels under slowed hydrogen exchange conditions. "Slowed hydrogen exchange conditions" are hereby defined as conditions wherein the rate of exchange of normal hydrogen for heavy hydrogen at amide hydrogens freely exposed to solvent is reduced substantially, i.e., enough to allow sufficient time to determine, by the methods described herein, the precise amide hydrogen positions which had been labeled with heavy hydrogen. The H-exchange rate is a function of temperature, pH and solvent. The rate is decreased three fold for each 10° C. drop in temperature. Hence use of temperatures close to 0° C. is preferred. In water, the minimum H-exchange rate is at a pH of 2–3. As conditions diverge from the optimum pH, the H exchange rate increases, typically by 10-fold per pH unit increase or decrease away from the minimum. Use of high concentrations of a polar, organic cosolvent shifts the pH min to higher pH, potentially as high as pH 6 and perhaps, with the right solvent, even higher.

At pH 2.7 and 0° C., the typical half life of a tritium label at an amide position freely exposed to solvent water is about 70 minutes. Preferably, the slowed conditions of the present inventions result in a half-life of at least 10 minutes, more preferably at least 60 minutes.

Tritium Exchange Embodiments

In one embodiment, the present invention contemplates the following procedure for characterization of a binding site or the high resolution identification of solvent-accessible peptide amide groups:

A. The phenomenon of hydrogen (tritium) exchange is used to substitute a radioactive probe (tritium) for each of the amide hydrogens on the amino acids which make up the surface of the receptor protein, including the surface of the receptor's ligand binding site. This labelling is accomplished under essentially physiologic conditions by incubating the receptor protein in solutions containing tritiated water. (Preferably, the water is of high specific activity.)

If one desires to characterize the binding site of the protein, the following steps (B) and (C) are performed.

B. Protein ligand (binding partner) is then added to the on-exchanged (tritiated) receptor protein and allowed to bind to its specific site on the receptor. Once the ligand has bound to the receptor, hydrogens on the amino acids which make up the surface of the receptor's binding site are no longer capable of efficiently interacting with the surrounding aqueous buffer, and further hydrogen exchange is markedly inhibited.

C. The tritiated receptor-ligand complex is then transferred to physiologic buffers free of tritium. Tritium label on the receptor-ligand complex is allowed to exchange off the receptor. However, binding complex-dependent hydrogen-bonding between the protein and binding partner and limited solvent accessibility to the protein-binding partner interface in the complex are selective impediments to the off-exchange of peptide amide tritium label sandwiched between the protein and binding partner. After the removal (off-exchange) of tritium from other regions of the protein-binding partner complex is substantially finished, the result is the preferential retention of tritium label at the amides for which hydrogen exchange is slowed by virtue of protein-binding partner interactions, typically amides proximate to amino acids which make up the surface of the receptor's ligand binding site. Optionally, the complex may be subjected to limited proteolytic digestion, denaturation and/or disulfide reduction while off exchange is proceeding, as long as the integrity of the binding protein: binding partner interaction is not substantially perturbed by such maneuvers.

Alternatively, the receptor ligand complex can be tritiated such that the peptide amide groups which compose the binding site and/or binding surface are not labeled and all other solvent-accessible peptide amide groups are selectively labeled. Thus, in this alternative embodiment, peptide amide groups which comprise the binding site and/or binding surfaces are "functionally labeled" by the absence of tritium.

D. The specific peptide bond amides which bear tritium are then identified. This is done by:

(1) shifting the labeled receptor-ligand complex to conditions (e.g., 0–4° C., pH 2.7) which dissociate the complex and at the same time slow down amide hydrogen exchange.

(2) optionally subjecting the receptor to proteolysis followed by reverse phase (RP) high pressure liquid chromatographic (HPLC) separation (preferably 2-dimensional) of the resulting receptor fragments under continued slow proton exchange conditions. Receptor fragments bearing tritium label are identified, isolated, and characterized as to their amino acid sequence, and therefore their location within the primary amino acid sequence of the intact receptor.

Preparation of the binding protein for proteolytic analysis may involve:

(a) trimming off of portions of the protein not required for complex formation;

(b) disruption of disulfide bonds which could complicate the analysis of the fragments (see section 5A); and/or (c) denaturation of the protein to render it more susceptible to proteolytic attack (see section 5B).

Step (a) may be performed before or after switching to slow hydrogen exchange conditions, since it does not cause dissociation of the contacting surfaces. Steps (b) and (c) are more likely to cause such dissociation and therefore will more often need to be performed under slow exchange conditions.

(3) determining the location of tritium label within the binding protein or each labeled peptide fragment from step (2) by subfragmenting the labeled binding protein or peptides (e.g., with acid-reactive carboxypeptidases or tritium-exchange-compatible chemical methods) under slow proton exchange conditions and characterizing the labelled subfragments. For example, the identity of each of the subfragments may be determined by amino acid analysis, peptide sequencing, or by comparison of their mobility with synthetic HPLC mobility marker peptides, and the amount of tritium label attached to each subfragment determined by scintillation counting. As each carboxy-terminal amino acid of the functionally labeled binding protein or peptide fragment is sequentially cleaved off by the carboxypeptidase, the nitrogen which formed the slowly-exchanging peptide amide in the intact peptide bond is converted to a rapidly exchanging secondary amine, and any tritium label at that nitrogen is lost from the peptide within seconds, whereas all other amide bond tritium remains in place. A stepdown in radioactivity from one subfragment to the next smaller one indicates that the amide just altered had been labeled with tritium.

In this manner, the precise location, within the protein, of each peptide amide that is functionally labeled by virtue of its solvent-accessibility and/or its interaction with its binding partner is determined. Inferentially, in this manner, the precise amino acids which make up the surface of the receptor and/or the surface of the receptor's binding site are then known. Studies may be performed to quantify the exchange rates of each of the labeled amides identified above both before and after complex formation with binding partner. This allows calculation of the magnitude of exchange slowing experienced by each of these amides consequent to complex formation, and allows optimization of on and off exchange times.

E. Parallel studies may be performed in which the cognate binding partner is on-exchanged with tritium, complexed with receptor protein, off-exchanged as a binding partner-protein complex and slowed amides in the binding partner identified as above. This procedure results in the identification of the subregions of the binding partner which interact with the protein.

F. The knowledge of the identity of the precise contact peptides in both receptor and ligand may be combined with additional structural information provided by the invention (identification of peptide amides of the protein and binding partner which are likely to directly form hydrogen bonds between protein and binding partner upon complex formation) to produce models for the complementary 3-dimensional structures of the receptor and ligand interaction surfaces. These models may then be used as the basis of the design and production of appropriate peptide and peptidomimetic drugs.

The individual steps of this procedure will now be considered in greater detail.

1. On-Exchange

The protein under study is incubated in buffer supplemented with tritiated water ($^3H_2O$), preferably of high specific activity. This results in the time dependent reversible incorporation of tritium label into every peptide amide on the surface of the protein, including its (potential) ligand binding subregion, through the mechanism of proton exchange.

Any physiologic buffer appropriate for the interaction of the protein with its binding partner may be utilized (with no constraints imposed on buffer pH or temperature). Suitable buffers include phosphate buffered saline (PBS), 0.15 mM NaCl, 10 mM $PO_4$, pH 7.4 PBS. The use of small incubation volumes (0.1–10 μl) containing high concentrations of receptor protein (10–100 mg/ml) is preferred.

The necessary level of tritiation (and hence the concentration of tritium in the buffer) is dependent on the total amount of protein available for analysis. For analysis of 1 mg protein, at least 10 Ci/ml is desirable; for 0.1 mg, 100 Ci/ml, and for 0.01 mg, 1000 Ci/ml. (Pure tritiated $H_2O$ is about 2500 Ci/ml.) For most applications, the tritiated water will be 50–500 Ci/ml. Without the use of these high specific activities, studies of proteins which are available in limited quantity would be much more difficult. (Even higher specific activity (e.g., 500–1,500 Ci/ml) may be used in the invention, but radiation safety considerations necessitate performance of such on- and off-exchange procedures in specialized facilities, such as are available in the tritium laboratory provided by the National Tritium Facility, Lawrence Berkeley Laboratories, University of California, Berkeley.)

It should be noted that with customary levels of tritium, only a small percentage of the binding protein molecules will be tritiated at any given exposed position. All that is required is that substantially each of the exposed amide hydrogen atoms be replaced in a detectable (by radiation counting) number of the binding protein molecules.

It is not necessary that the tritium exchange analysis rely on only a single choice of "on-exchange" time. Rather, the skilled worker may carry out the experiment using a range of on-exchange times, preferably spanning several orders of magnitude (seconds to days) to allow selection of on-exchange times which allow efficient labeling of the various peptide amides present in the protein, which will become slowed in their exchange rate consequent to the interaction of the protein to its binding partner, and at the same time minimize background labeling of other amide positions after off-exchange is completed (see section 10 below).

2. Receptor-Binding Partner Complex Formation

After a suitable period of tritium on-exchange, the protein's binding partner is added to the tritiated protein-buffer solution and the two allowed to form a binding complex. The binding partner is preferably added in quantities sufficient to produce saturation binding to the protein (usually equimolar amounts) and at high concentrations (e.g., 10–100 mg/ml) to maximize the rate and extent of binding. To minimize tritium labeling of the added binding partner by proton exchange (important when utilizing short on-exchange times), $^3H_2O$ in the buffer is preferably diluted with tritium-free buffer (10–1000 fold dilution) within 0–100 seconds of binding partner addition. Additional manipulations detailed below may be used at this step to further minimize incorporation of tritium label into the binding partner.

3. Off-Exchange

The tritiated protein-binding partner complex is then transferred to physiologic buffers identical to those employed during on-exchange, but which are substantially free of tritium. Tritium label on the protein then exchanges off the protein at rates identical to its on-exchange rate everywhere except at amides which have been slowed in their exchange rate by virtue of the interaction of protein with binding partner. With sufficient off-exchange time, the result is the specific retention of tritium label at each of the peptide amide bonds which occur between the amino acids which make up the surface of the protein's binding site for the binding partner. We refer to this process as a complex formation-dependent functional labeling of the protein with tritium. At least 90%, more preferably, at least 95%, 96%, 97%, 98% or 99% or more, of on-exchanged tritium label at other sites is off-exchanged from the protein.

In general, off-exchange is allowed to proceed for 5 to 50 times, more preferably about 10 times longer than the on-exchange period, as this allows off-exchange from the protein of greater than 99% of the on-exchanged tritium label which has not experienced a slowing of exchange rate subsequent to the protein's interaction with binding partner. Preliminary studies may be performed with the protein and binding partner to determine the on and off exchange times which optimize the signal (tritium remaining in functionally labeled amides) to noise (tritium remaining in background amides) ratio (see section 8).

In preferred embodiments, the off-exchange procedure may be performed with the use of Sephadex G-25 spin columns prepared and utilized as described in Example 1 (below), by G-25 column chromatography as described by Englander (6,19) or by use of perfusive HPLC supports that allow rapid separation of peptide/protein from solvent (Poros® columns, PerSeptive Biosystems, Boston, Mass.). Use of the G-25 spin columns allows the separation of the complex from greater than 99.9% of buffer tritium. Residual buffer tritium and tritium off-exchanged from the complex may optionally be further removed by dialysis of the complex against tritium free buffer during off exchange.

Alternatively, complex formation and off-exchange can be accomplished by first reacting the on-exchanged protein-buffer mixture with binding partner which has been covalently attached to a solid support (e.g. binding-partner-Sepharose), allowing the on-exchanged protein to complex to the solid-phase binding partner, followed by washing of the sepharose-binding partner-protein conjugate with tritium free buffer. Alternatively, soluble protein-binding partner complexes may be formed as above, and captured with a solid phase adsorbent that can bind to either the protein or binding partner component of the complex (e.g. Sepharose with covalently attached antibodies specific for protein or binding partner).

Most protein-ligand binding interactions that will be probed with this technique are reversible reactions: binding partner will dissociate from and rebind to the protein during the off-exchange period, and during the brief intervals where the protein's binding site is unoccupied with binding partner, proton off-exchange proceeds at the unprotected rate. It is therefore important to minimize the time that the binding site is unoccupied. In a preferred embodiment, this is accomplished by having both receptor and binding partner present at high concentration, e.g., at least mg/ml concentrations, up to 100 mg/ml concentrations each throughout the off-exchange period, and performing the on and off exchange reactions at temperatures at or below room temperature, preferably 4° C.

4. Trimming of the Binding Protein (optional)

Prior to dissociation of the complex, e.g., during the off-exchange period, which typically lasts hours to days, the complex may optionally be chemically or enzymatically treated to produce the smallest fragment of protein which is still capable of remaining tightly bound to the binding partner, and this residual "trimmed" complex isolated. Removal of portions of the protein not essential for continued complex formation will decrease the number of background peptides generated during the subsequent acid proteolysis of the trimmed complex (Section 6). This predigestion and purification can be performed with a wide variety of proteases (e.g. trypsin, pronase, V-8 protease chymotrypsin proteinase-K) as well as certain chemical agents (e.g., cyanogen bromide, iodosobenzoic acid), and under virtually any conditions of induced partial protein denaturation (e.g. urea, guanidinium chloride sodium dodecyl sulfate, non-ionic detergents, reductants such as 2-mercaptoethanol, dithiothreitol), ionic strength, temperature, time and pH which do not substantially dissociate the contacting surfaces of the protein-binding partner complex. Excessive digestion efforts which result in dissociation of these surfaces from each other will cause a large fraction of functional tritium label to be immediately off-exchanged, as greater than 50% of peptide amides in the dissociating surfaces will have exchange half-lives of less than 1 minute at approximately 15 pH 7. The goal is to generate and isolate a fragment of the protein, preferably 15–100 kD in size more preferably 15 kD, which remains attached to the binding partner. Often "ligand stabilization" of proteins which are proteolysed while bound to binding partner allows the continued binding of the protein fragments to partner.

Preliminary studies may be performed with the off-exchanged complex to determine conditions which result in a suitably trimmed protein-binding partner complex. In a preferred embodiment, the quantity of residual tritium functionally bound to the intact off-exchanged complex is first determined by measurement of tritium which migrates with the void volume (Mr>10,000 kD) on a G-25 spin column (pH 7.4). Aliquots of the complex are then subjected to varied fragmentation conditions, and the fraction of tritium label which remains attached to polypeptides under each digestion condition (migrates with G-25 void volume) determined. The proteolytic products of the most vigorous digestions which "release" less than 5% of complex-associated tritium are (as per Section 5) adjusted to pH 2.7, 0° C., subjected to RP-HPLC at pH 2.7, 0° C., and peptides/protein fragments which bear label identified, isolated, and their molecular weights determined by SDS-PAGE. The labeled proteolytic products produced in these limited digests are likely to be large polypeptides, and therefore RP-HPLC supports suitable to the purification of such peptides (C-4, phenyl columns) are utilized. Alternatively, when solid-phase adsorbents are used for complex formation/off-exchange (step 3), proteolysis as above, now of the solid phase binding partner-protein complex, is allowed to proceed as extensively as possible without release from the solid support of greater than 5% functionally attached tritium. The predigested protein/complex is then released from the immunoadsorbent with denaturants including a shift to pH 2.7, and the predigested protein further proteolysed with pepsin other acid reactive proteases.

A binding protein may also be trimmed earlier, e.g., before "on-exchange" or before complex formation, provided that the trimmed protein binds the partner sufficiently similarly to the original protein to be of interest.

5. Switch to Slow Amide Hydrogen Exchange Conditions

The protein-binding partner complex (or predigested complex—see Step 4) or selectively labeled protein in the case of alternative embodiments of the invention wherein the positions of solvent accessible peptide amide protons are to be determined in the absence of a binding partner, is then shifted to conditions of temperature and pH which greatly slow the half life of peptide amide hydrogen exchange, and essentially "freeze" in place the tritium labels. In a preferred embodiment, the complex is shifted to 0° C., and pH 2.7 conditions under which the half life of exchange of peptide amide label in fully denatured peptides is at least 70 minutes. The label will be sufficiently held in place under these conditions so that several rounds of proteolytic fragmentation, HPLC separation, and tritium quantification can be performed without unacceptable loss of label.

For some binding proteins, switching to slow hydrogen exchange conditions is sufficient to cause dissociation of the complex. If not, a dissociating agent, such as a chaotropic agent may be added.

5A. Disruption of Disulfide Bonds (optional)

High resolution localization of tritium label-bearing amides requires the proteolytic generation of peptides less than approximately 15–20 amino acids in size under conditions which allow the label to remain in place (e.g., 0° C., pH 2.7). The ability of any protease to fragment a protein or peptide is limited by the accessibility of the protease to susceptible peptide bonds. While denaturants such as acidic pH, urea, detergents, and organic co-solvents can partially denature proteins and expose many otherwise structurally shielded peptide bonds, pre-existing disulfide bonds within a protein can prevent sufficient denaturation with these agents alone. In conventional protein structural studies, disulfides are usually cleaved by reduction with 2-mercaptoethanol, dithiothreitol, and other reductants which unfortunately require a pH greater than 6 and elevated temperature for sufficient activity, and are therefore not useful for the reduction of disulfides at pH 2.7 or below. For this reason, the tritium exchange art has not attempted any form of disulfide bond disruption, has for the most part been restricted to the study of proteins without intrinsic disulfide bonds, and has accepted the low resolution achievable without disulfide bond disruption. The applicant has recognized and demonstrated that acid-reactive phosphines such as Tris (2-carboxyethyl) phosphine (TCEP) (31–36) can be used to disrupt disulfides under the acidic pH and low temperature constraints required for tritium exchange analysis (see FIGS. 7a–j). These manipulations disrupt these associations and at the same time continue to produce a markedly slowed proton exchange rate for peptide amide protons.

5B. Protein Denaturation. (optional)

In previous studies by Englander et al. and others, employing medium resolution tritium exchange, proteolytic fragmentation of tritium-labelled proteins under slowed-exchange conditions was accomplished by shifting the protein's pH to 2.7, adding high concentrations of liquid phase pepsin, followed by brief (10 min.) incubation at 0° C. With the proteins studied by Englander et al. simply shifting pH from that of physiologic (7.0) to 2.7 was sufficient to render them sufficiently denatured as to be susceptible to pepsin proteolysis at 0° C. Furthermore, these proteins, in general, did not contain disulfide bonds that interfered with effective denaturation by such (acid) pH conditions or contain disulfide bonds within portions of the protein under study with the technique. The applicant has found that other proteins (for example hen egg lysozyme) are negligibly denatured and are not substantially susceptible to pepsin proteolysis when continuously incubated at comparable acidic pH and depressed temperature (10–0° C.). This is the consequence of the existence of a thermal barrier to denaturation for many proteins incubated in many denaturants; i.e., denaturation of proteins at lower temperatures (10–0° C.) is often inefficient and a slow process, incompatible with the requirement of medium resolution tritium exchange techniques that manipulations be performed rapidly, such that the attached tritium label is substantially retained at functionally labelled amides of the binding protein.

The applicant has discovered that such proteins become extraordinarily susceptible to pepsin proteolysis at 0° C. when they are treated with the sequential denaturation procedure described below. Furthermore, the applicant has discovered that although TCEP can effect the reduction of disulfide bonds in proteins at 0° C. and pHs in the range of 2–3, it is relatively inefficient at doing so under these conditions and becomes much more efficient at effecting reduction at a pH of 5.0 or greater. Conditions can be arranged to greatly increase the efficiency of TCEP-mediated reduction while at the same time preserving slow exchange conditions. This is accomplished by simultaneously denaturing the protein with guanidine thiocyanate, employing very high concentrations of TCEP and raising the pH of the solution to 5.0. While this pH would normally produces an unacceptable 100-fold increase (as compared to that at pH 2.7) in the rate of loss of tritium from the labelled protein, the elevated pH-induced increase in the rate of tritium loss is substantially offset by limiting the water content of the incubation mixture (and thereby markedly slowing the rate of tritium loss) when the protein is being reduced at pH 5.0, and the solution pH then is shifted back to pH 2.7 once reduction is complete. The result is effective reduction of proteins at a pH of 5 and 0° C. with substantially complete retention of tritium label on the binding protein.

The denatured (or denatured and reduced) protein solution is then passed over a pepsin-agarose column, resulting in efficient and rapid fragmentation of the protein (in $\leq 1$ min.). The fragments can be, and usually are, immediately analyzed on RP-HPLC without unnecessary contamination of the peptide mixture with the enzyme pepsin or fragments of the enzyme pepsin. Such contamination is problematic with the technique as taught by Englander, et al., as high concentrations of pepsin (often equal in mass to the protein under study) are employed, to force the proteolysis to occur sufficiently rapidly at 0° C.

While proteins are often subjected to purposeful denaturation with agents other than a pH shift prior to digestion with pepsin, this has never been done at depressed temperatures (10–0° C.) before, and the applicant has discovered that while guanidine thiocyanate at the indicated concentrations is sufficient to suitably denature and render susceptible to pepsin proteolysis proteins at 10–0° C., several other strong denaturants, including urea, HCl, sodium dodecyl sulfate (SDS) and guanidine HCl, were, at least when used alone, unable to adequately denature lysozyme at these low temperatures. However, the concentrations of guanidine thiocyanate required for such denaturation are incompatible with pepsin digestion; i.e., they denature the pepsin enzyme before it can act on the denatured binding protein. When the guanidine thiocyanate is removed (at 10–0° C.) from the solution after protein denaturation has been accomplished in an attempt to overcome this inhibition of pepsin activity, the protein rapidly refolds and/or aggregates, which renders it again refractory to the proteolytic action of pepsin. The applicant has discovered that if proteins are first denatured in $\geq 2M$ guanidine thiocyanate at 0° C. and the concentration of thiocyanate then reduced to $\leq 2M$ while at the same time the guanidine ion is maintained $\geq 2M$ (by diluting the guanidine thiocyanate into guanidine hydrochloride), the denatured protein remains in solution, remains denatured, and the enzyme pepsin is efficiently proteolytically active against the denatured protein in this solution at 0° C. The stability of pepsin-agarose to this digestion buffer is such that no detectable degradation in the performance of the pepsin column employed by the applicant has occurred after being used to proteolyze more than 500 samples over 1 years. No pepsin autodigestion takes place under these conditions.

Denaturation without concomitant reduction of the binding protein may be accomplished by contacting it (at 0–5° C.) with a solution containing $\geq 2$ molar guanidine thiocyanate pH 2.7, followed by the addition of an equal volume of 4 molar guanidine hydrochloride pH 2.7.

Denaturation with disulfide reduction may be accomplished by contacting the binding protein with a solution containing $\geq 2$ molar guanidine thiocyanate, 0.3–0.7 molar TCEP, 5–20% $H_2O$ (by volume), with the balance of volume being acetonitrile, dimethyl sulfoxide, or other water miscible nonaqueous solvent in which the denaturant (e.g. guanidine thiocyanate) and disulfide bond disrupting agent (e.g., TCEP), if used, remain soluble at substantially these concentrations, and such that the solvent system does not freeze at the "slow exchange" temperature. The pH of the solution is preferably in the range of 4.8–5.2, optimally 5.0. After this incubation, 2 volumes of a 2.5 molar guanidine hydrochloride solution is added, with the pH and buffering capacity of the solution such as to achieve a pH of 2.7 in the final mixture.

Denatured (with or without reduction) binding protein is then passed over a column composed of insoluble (solid state) pepsin, whereby during the course of the passage of such denatured or denatured and reduced binding protein through the column, it is substantially completely fragmented by the pepsin to peptides of size range 1–20 amino acids at 0° C. and at pH 2.7. The effluent from this column (containing proteolytically-generated fragments of binding protein) is directly and immediately applied to the chromatographic procedure employed to separate and isolate protein fragments, preferably analytical reverse-phase HPLC chromatography.

It should be noted that denaturants, besides rendering the binding protein more susceptible to proteolysis, also help dissociate it from its partner.

6. Generation of Peptide Fragments (Optional)

To ultimately localize the protein's amides which are functionally labeled with tritium, small peptides bearing the retained tritium label (preferably, 5–25 amino acids in size) are optionally proteolytically generated from labeled protein and separated from the many other unlabeled peptides generated by fragmentation of the protein, all under conditions which minimize off-exchange of amide tritium from the peptide. Small peptides have little secondary structure and therefore their amides are free to exchange with solvent hydrogen. If tritium label is to remain in place on such peptides, proteolysis and purification (e.g., RP-HPLC) conditions must be adjusted to slow such off-exchange.

The labeled and dissociated binding protein is therefore fragmented under slow H-exchange conditions, e.g., by proteolysis with high concentrations of a protease which is stable and active with the aforementioned conditions (e.g., pH 2.7, 0° C.). Suitable acid tolerant proteases include pepsin (19), cathepsin-D (37) Aspergillus proteases (37a–37c), thermolysin (38) and mixtures of these proteases. In a preferred embodiment, pepsin is used, preferably at a concentration of 10 mg/ml pepsin at 0° C. pH 2.7 for 5–30 minutes, preferably 10 minutes.

Other physical and chemical fragmentation methods may be used provided they are (1) are compatible with slow H-exchange conditions, (2) do not cause shifts in the positions of the amide labels, and (3) produce a reasonable number of fragments from the protein of interest.

Preferably, prior to fragmentation of the binding protein, binding partner (if susceptible to the fragmenting agent) is removed, so as not to complicate purification with binding partner fragments.

6A. Purification of Fragments

As acid proteases in general have very broad cleavage specificity, they fragment the protein into a very large number of different peptides. In most protein-binding partner systems studied by tritium exchange, it is likely that the interacting binding surfaces will contain roughly 10–20 tritium labeled peptide amide which upon proteolysis will result in approximately 1–5 label-bearing peptides, the precise number depending on the inherent fragmentation mode of the protein under study with the proteases utilized. The number of "background," non-labeled peptides (derived from regions of the protein and binding partner that do not participate in the binding interaction) generated by the fragmentation procedure will be a direct function of the size of the protein. Background peptides will be present in the proteolytic digest in numbers 10–1,000 times greater than will be functionally labeled peptides when proteins with sizes in the range of 30–200 kD are proteolyzed.

This large number of background peptides causes two difficulties: First, they must all be cleanly separated from the functionally labeled peptides to allow identification of the label-bearing peptides. Second, background peptides contain small amounts of tritium label and even though the amount of label per background peptide is generally less than 1% of that of functionally labeled peptides, background peptides are present in much greater amounts and are likely to obscure the presence of functionally labeled peptides and analytical separation.

Given these considerations, only proteins less than 30 kD in size have been successfully characterized in the past by medium resolution tritium exchange. Upon acid proteolysis of larger proteins, so many different fragments would be obtained that individual fractions obtained on a single HPLC separation performed at pH 2.7 would be unacceptably contaminated with background peptides.

Any method of purifying the fragments which is capable of resolving the mixture while maintaining slow H exchange condition is acceptable. The preferred method is high pressure liquid chromatography (HPLC), especially in reverse phase (RP). (An alternative method is that of mass spectroscopy.)

The art has overstated the sensitivity of the tritium label to pH. Englander (10) reported that at 0° C., the tritium label was most stable (when the tritiated protein was placed in an untritiated aqueous buffer) at pH 2.7, and that the rate of off-exchanged increased rapidly (10 fold per pH unit) as one moved away from that pH. Surprisingly, Applicant found that at 0° C., the label was sufficiently stable to permit analysis even at a pH of 2.1. While the acceptable pH range will vary with temperature, and the choice of solvent (the optimal pH increases if a polar nonaqueous solvent is introduced), the fact remains that pH was previously considered to be essentially fixed. Since the tritium label is stable over a broader pH range, such as 2.1–3.5, it is possible to depart from Englander's recommended pH of 2.7 in seeking HPLC conditions which result in effective separation of the peptide fragments.

When the binding molecules are large, so many different fragments are obtained after proleolytic digest that some of the individual peaks on a single HPLC separation, even at optimized ph, may be heterogeneous.

RP-HPLC resolution of co-migrating multiple peptides may be greatly improved by resorting to a two-dimensional RP-HPLC separation in which two sequential RP-HPLC separations are performed at substantially different pH's, e.g. 2.7 and 2.1.

A two-dimensional HPLC separation allows high efficiency purification of tritium label bearing-peptides from the enormous number of unlabeled peptides generated by peptic fragmentation of large proteins. Two-dimensional separation of molecules is known in the chromatographic art. However, despite frequent complaints in the Tritium exchange literature about resolution problems, 2D separations have not been employed previously in connection with Tritium exchange.

In a preferred embodiment of the invention, tritium-labeled protein fragments are first separated by means capable of sufficiently resolving the fragments, such as by RP-HPLC (utilizing any of a number of potential chromatographic support including C4, C18, phenol and ion exchange, preferably C18). This separation may be performed at pH 2.1–3.5 and at 4–0° C., more preferably, at pH 2.7 and 0° C., which may accomplished by employment of any buffer systems which operate at this pH, including citrate, chloride, acetate, more preferably phosphate. Peptides are eluted from the reverse phase column with a similarly buffered gradient of polar co-solvents including methanol, dioxane, propanol, more preferably acetonitrile. Eluted peptides are detected by on-line ultraviolet light absorption spectroscopy performed at frequencies between 200 and 300 nm, preferably 214 nm. Tritium label is detected by scintillation counting of a sampled fraction of the HPLC column affluent. Peptides bearing label that has been specifically protected from off-exchange by complex formation with binding partner are identified by comparing the specific activity of each labeled peptide to the specific activity of the same peptide prepared from protein subjected to identical on/off exchange, proteolysis and HPLC conditions, but which have been off-exchanged without added binding partner.

HPLC fractions containing peptides with such functionally labeled amides are then subjected to a second dimension RP-HPLC separation which may be performed at pH 2.1–3.5 and 4–0° C., more preferably, at pH 2.1 and 0° C., accompanied by any buffer systems which operates at this pH, including citrate, chloride, acetate, phosphate, more preferably TFA (0.1–0.115%). Peptides are eluted from their reverse phase column with a similarly buffered gradient of polar co-solvents including methanol, dioxane, propanol, more preferably acetonitrile. Eluted peptides are detected, tritium measured and functionally labeled peptides identified as in the first HPLC dimension described above. Functionally labeled peptides are isolated (collection of the appropriate fraction of column effluent), water, acetonitrile, and TFA removed by evaporation, and the remaining purified peptides each characterized as to its primary amino acid structure by conventional techniques, e.g., amino acid analysis of complete acid hydrolysates or gas-phase Edman degradation microsequencing. Reference is then made to the previously known amino acid sequence of the intact protein to infer the location of the tritium-labeled peptides within the intact protein's primary sequence. Employment of TFA buffer in the second dimension has the additional advantage that no residual salt (i.e. phosphate) remains after solvent evaporation. Residual phosphate frequently interferes with the chemical reactions required for amino acid analysis and Edman degradation, a problem obviated by the use of volatile TFA in the second dimension buffer.

Most preferably, proteolytic digests are first separated at pH 2.7 in phosphate buffered solvents and each eluted peptide peak fraction which contains tritium-labeled amides is identified, collected, and then subjected to a second HPLC separation performed in trifluoracidic acid (TFA)-buffered solvents at pH 2.1.

7. High Resolution Sublocalization of Labeled Amides Within Label-Bearing Peptides To routinely localize peptide amide tritium label to the single amino acid level, applicant systematically cleaves every peptide bond within the labeled protein or a purified label-bearing peptide fragment. Slow H-exchange conditions must be used for this proteolysis as the small peptides generated have no stable conformational structure and rapid loss of tritium label from the amides would occur if rates of exchange were not slowed, e.g., by ambient acidic pH.

Most known acid-reactive proteases cleave peptides in a basically nonspecific manner similar to that of pepsin; studies employing other pepsin-like proteases have not proved to be of significant utility in increasing resolution of labeled amides.

A special class of acid-reactive proteases, the carboxypeptidases, are able to generate all required subfragments of labeled protein or pepsin-generated peptides in quantities sufficient for high resolution tritium localization. Many carboxypeptidases are active at pH 2.7 and sequentially cleave amino acids from the carboxy terminus of peptides. Such enzymes include carboxypeptidase P, Y, W, and C (39). While carboxypeptidases have been used for limited carboxy-terminal sequencing of peptides, often at pH in the range of 2.7 (40), their use in tritium exchange techniques has not been disclosed. The need to minimize tritium losses forbids the use of carboxypeptidases which are inactive in acidic (pH 2.7) buffers, such as carboxypeptidases A and B. However, carboxypeptidase-P, Y, and several other acid-reactive carboxypeptidases (W,C) are suitable for proteolysis of peptides under acidic conditions (39). The tritium exchange art has failed to recognize the utility of carboxypeptidases to tritium exchange studies, possibly because the carboxypeptidases are even more nonspecific in the types of peptide bonds they cleave than are pepsin-like proteases and therefore might have been thought to result in inadequate recovery of any single subfragment.

Furthermore, chemical procedures employing pentafluoropropionic anhydride can produce sets of C-terminal-truncated peptide fragments under slowed amide exchange conditions (see below, 41,42).

In the preferred embodiment, tritium-exchange-labeled proteins are nonspecifically fragmented with pepsin or pepsin-like proteases, the resulting tritium-labeled peptides isolated by two-dimensional HPLC and these in turn exhaustively subfragmented by controlled, step-wise digestion with acid-(i.e., enzymatically active under acidic conditions) exopeptidases and/or by chemical means (see below). These digests are then analyzed on RP-HPLC performed at 0° C. in TFA-containing buffers (pH 2.1) and each of the generated subfragments (typically 5–20) is then identified. The identity of each of the several subfragments maybe determined by any suitable amino acid analysis, peptide sequencing, or through the use of synthetic HPLC mobility marker peptides, and the amount of tritium label attached to each subfragment truncated peptide determined by scintillation counting. In this manner, the precise location, within the protein, of each peptide amide that is functionally labeled with tritium by virtue of its interaction with binding partner is determined. By consideration of the tritium content of each of the identified subfragments the amide hydrogens which had been replaced by tritium during the "on-exchange" step may be inferred. It should be noted that the purpose of the carboxypeptidase treatment is to generate the subfragments; the method does not require use of carboxypeptidase to sequence the fragments or subfragments. Preferably, the sequence of the binding protein, or at least of the material portion thereof, is known prior to commencement of the present method. However, it may be determined at any time, even after the subfragmentation, although the data gleaned from the subfragmentations cannot be properly interpreted until the sequences of a least the source is known.

Controlled sequential carboxy-terminal digestion of tritium-labeled peptides with carboxypeptidases can be performed under conditions which result in the production of analytically sufficient quantities of a set of carboxy-terminal truncated daughter peptides each shorter than the preceding one by from one to about 5 carboxy-terminal amino acid residues, preferably by a single carboxy-terminal amino acid. As each carboxy-terminal amino acid of the functionally labeled peptide is sequentially cleaved by the carboxypeptidase, the nitrogen which formed the slow-exchanging peptide amide in the intact peptide bond is converted to a rapidly exchanging secondary amine, and any tritium label at that nitrogen is lost from the peptide within seconds, even at acidic pH. A difference in the molar quantity of tritium label associated with any two sequential subpeptides implies that label is localized at the peptide bond amide which differs between the two subpeptides.

In a preferred embodiment, synthetic peptides are produced (by standard peptide synthesis techniques) that are identical in primary amino acid sequence to each of the functionally labeled pepsin-generated peptides identified in Step 6. The synthetic peptides may then be used in preliminary carboxypeptidase digestion (pH 2.7, 0° C.) and HPLC (in TFA-buffered solvents) studies to determine; 1) the optimal conditions of digestion time and protease concentration which result in the production and identification digestion on all possible carboxypeptidase products of the peptide under study; and 2) the HPLC elution position (mobility) of each carboxypeptidase-generated subfragment of synthetic peptide.

To facilitate this latter procedure, a set of reference peptides may be produced consisting of all possible carboxyterminal truncated daughter peptides which an acid carboxypeptidase could produce upon digestion of a "parent" peptide. These serve as HPLC mobility identity standards and allow the deduction of the identity of daughter peptides actually generated by carboxypeptidase digestion. Certain daughter peptides may be enzymatically produced in quantities insufficient for direct amino acid analysis or sequencing, but their HPLC mobility can be measured and compared to that of the synthetic peptides. Peptides can be detected and quantified by standard in-line spectrophotometers (typically UV absorbance at 200–214 nM) at levels well below the amounts needed for amino acid analysis or gas-phase Edman sequencing.

After these preliminary studies, the pepsin-generated HPLC isolated, functionally labeled peptide (prepared in Step 6) is then carboxypeptidase digested and analyzed under the foregoing experimentally optimized conditions, the identity of each fragment determined (by peptide sequencing or by reference to the mobility of reference peptide mobility marker) and the amount of tritium associated with each peptide subfragment determined.

Alternatively, a chemical technique may be used for the successive carboxy terminal degradation of peptides under slowed tritium exchange conditions. Tritium-labeled peptides in HPLC buffers are held at −35° C. and solvents removed by cryosublimation (40a, 40b; vacuum at 1–20 millitorr, solvents collected in a liquid nitrogen trap). The dried peptide is then reacted with vapor phase pentafluoropropionic acid anhydride (PFPA) as described in (54, 55)

except that the peptide temperature is kept at −35° C. for times up to 3 hours. PFPA is then removed by vacuum and the fragmented peptide made to 50 mM $PO_4$ pH 2.7, and analyzed by HPLC.

In general, the known aminopeptidases are not able to sequentially degrade a peptide under slow hydrogen exchange conditions. However, if an acid-reactive aminopeptidase is discovered in nature, or produced by mutation of a known aminopeptidase, there is no reason that an aminopeptidase can not be used in place of the presently preferred carboxypeptidase. In that event, the stepwise degradation will begin at the N-terminal, rather than the c-terminal, of each analyzed peptide fragment.

It should be noted that by using polar, nonaqueous high concentrations of cosolvents to shift the $pH_{min}$ of the H-exchange rate, a greater variety of reagents may be used than would otherwise be the case. A cosolvent of particular interest in this regard is glycerol (or other polyols), as it is unlikely to denature the enzyme when employed at the high concentration to substantially shift the pH min.

8. Optimization Of On and Off Exchange Times

Each peptide amide hydrogen associated with the protein-binding partner interaction surface has a unique exchange rate with solvent tritium in the native folded, unliganded state, which is then shifted to another distinct exchange rate once protein-binding partner complex formation has occurred. The signal to noise ratio (ratio of tritium functionally bound to this peptide amide over total background tritium bound to all other peptide amides in the protein) can be optimized by a knowledge of the exchange rates of this amide hydrogen in the native unliganded protein and in the protein-binding partner complex.

An amide hydrogen with an exchange half-life of one minute in the protein's native, unliganded state and 10 minutes in the liganded state might be optimally studied by on-exchanging the receptor protein for 2 minutes (2 half-lives of on-exchange time will result in incorporation of tritium at 75% of the maximal possible equilibrium labeling of the peptide amide) followed by 10 minutes of off-exchange in the liganded state (50% of on-exchanged label will remain on the functionally labeled peptide amide and less than 0.1% of on-exchanged label will remain on each of the background labeled peptide amides).

To measure the exchange rates of a particular functionally labelable peptide amide as it exists in the native, unliganded protein, aliquots of protein are on-exchanged for varying times (0.5 seconds to 24 hours), bound to binding partner, and then off-exchanged for a fixed time, preferably 24 hours. After pH 2.7, 0° C. proteolytic digestion and HPLC separation, radioactivity associated with the peptide fragment containing the peptide amide under study is measured. The amount of the radioactivity which represents background (amides which are not functionally labeled) is determined by measuring the amount of label associated with the same peptide when the protein is on-exchanged for the same duration but off-exchanged for 24 hours in the absence of added ligand prior to proteolysis and HPLC analysis. Specific radioactivity associated with the amide is determined as a function of on-exchange time, and the half-life of (on) exchange of the amide in the unliganded protein calculated.

To determine the exchange rate of the same peptide amide when it is in the protein-binding partner complex, protein is on-exchanged for a fixed, long period of time (preferably 24 hrs) complexed with binding partner, off-exchanged for varying times (preferably 10 seconds to 4 days), acid proteolysed, and HPLC analyzed as above. Specific radioactivity associated with the amide is determined as a function of off-exchange time, and the half-life of (off)-exchange of the amide in the liganded protein calculated. With this information the times of on and off-exchange are adjusted to optimize the signal/noise ratio for each of the amides functionally labeled in the protein-binding partner system under study.

9. Modeling of Receptor-Ligand Contact Surfaces

Studies identical in design to those described above (1–8) may also be performed on the corresponding binding partner protein (the binding partner protein is on-exchanged, liganded to receptor protein, off-exchanged, etc.), resulting in the identification of the amides of the binding partner which are slowed in exchange by virtue of interaction with receptor protein. The knowledge of the identity of the precise contact peptides in both protein and binding partner may be used to produce computer-assisted models for the complementary 3-dimensional structures of the protein and binding partner surfaces.

Construction of these models is aided by additional information provided by the invention which allows the identification of a subset of peptide amides on the protein's binding surface which are likely to form hydrogen bonds with acceptor residues on the cognate binding protein contact surface. While most of the peptide amides present on the native, uncomplexed protein or binding partner interaction surfaces can be expected to be hydrogen bonded to other portions of the same protein, a fraction of these peptide amides, possibly approaching 50%, may be hydrogen bonded only to solvent. As most protein-binding partner contact surfaces are highly complementary to each other, it is likely that upon complex formation solvent water is removed from the interaction surfaces, and amides previously hydrogen bonded to water will form new hydrogen bonds to the complementary surface of the partner. This subset of binding surface amides is readily identified in our studies (Step 8) as they will have an exchange rate in the protein's native, unliganded state of 0.5 seconds at pH 7.0 and 0° C. These amides can form hydrogen bonds with the complementary surface only if their hydrogens are oriented in the direction of the complementary surface. This in turn places orientation constraints on the entire associated peptide bond and to a lesser degree the side chains of the two flanking amino acid residues of each such amide. Application of these constraints to the foregoing models of interaction surface structure allow higher resolution modeling of the 3-dimensional structure of the protein-binding partner ligand interaction surfaces.

10. Automation of the Procedures Required for the Performance of Enzymatic Degradation and HPLC Analysis Under Slowed Tritium Exchange Conditions While digestion and analysis procedures are performed at 0° C., analytical samples of tritium exchange-labeled peptides must be stored at temperatures of approximately −60 to −80° C. if unacceptable losses of label from the peptide are to be avoided over intervals of hours to weeks. Tritium exchange continues in frozen samples in a manner inversely related to temperature but effectively stops at temperatures of approximately −70° C. At present, tritium exchange analysis is performed by manually removing samples from −70° C. storage, melting them manually at 0° C., manual addition of reagents (buffers, enzymes) and manual injection of samples onto the HPLC column. These manipulations are labor intensive and expose the samples to inadvertent heating during handling. If HPLC-separated peptides are to be collected and stored for future study, they are manually collected and stored at −70° C. No presently available robotic HPLC autosampler has the capability of performing the necessary manipulations on samples stored in the frozen state.

A Spectraphysics AS3000® autosampler may be modified so as to allow automation of these steps. These preferred modifications were: inclusion of a solid dry ice bath in which samples are stored until analysis; use of modified fluidic syringes which operate reliably at 0° C.; control of the autosampler by an external computer; and placement of the autosampler HPLC column and spectrophotometer within a 0° C. refrigerator. Under computerized control, the autosampler's mechanical arm lifts the desired sample from the −70° C. bath, and places it in a heater/mixer which rapidly melts the sample at 0° C. The liquified sample is then automatically injected onto the HPLC column. Operation of HPLC pumps, on-line radiation counter and data acquisition is similarly automated.

To collect tritium-labeled, HPLC-separated peptides under slowed exchange conditions, a Gilson-303® fraction collector (also present in the 0° C. refrigerator) has been modified so that the sample collection tubes are immersed in a dry ice bath. Computer-directed diversion of desired HPLC effluent fractions into these prechilled tubes results in rapid freezing of the desired tritium-labeled peptides to −70° C.

Deuterium Exchange Embodiments

In another embodiment, functionally labeled proteolytic fragments, generated from a protein that has been functionally labeled with deuterium (rather than tritium) prior to receptor-ligand complex formation, are analyzed by mass spectroscopy, conducted under conditions which minimize off-exchange of peptide amide deuterium from peptide fragments and allow the direct determination of the location of functionally attached label within a peptide in the size range 3–30 amino acids.

Mass spectroscopy has become a standard technology by which the amino acid sequence of proteolytically generated peptides can be rapidly determined (43). It is commonly used to study peptides which contain amino acids which have been deuterated at carbon-hydrogen positions, and thereby determine the precise location of the deuterated amino acid within the peptide's primary sequence. This is possible because mass spectroscopic techniques can detect the slight increase in a particular amino acid's molecular weight due to the heavier mass of deuterium. McCloskey, et al (44) discloses use of deuterium exchange of proteins to study conformational changes by mass spectrometry.

The applicant has devised a deuterium-exchange technique essentially identical, in steps 1–5, to the tritium exchange technique described above except that on-exchange is performed in deuterated water (preferably 80–99% mole fraction deuterated water). This modified procedure, after addition of binding partner and off-exchange, specifically labels with exchanged deuterium the peptide amides which make up the interaction surface between protein and binding partner. Proteolytically generated fragments of protein functionally labeled with deuterium are identified, isolated, and then subjected to mass spectroscopy under conditions in which the deuterium remains in place on the functionally labeled peptide amides. Standard peptide sequence analysis mass spectroscopy can be performed under conditions which minimize peptide amide proton exchange: samples can be maintained at 4° C. to zero degrees C with the use of a refrigerated sample introduction probe; samples can be introduced in buffers which range in pH between 1 and 3; and analyses are completed in a matter of minutes. MS ions may be made by MALDI (matrix-assisted laser desorption ionization) electrospray, fast atom bombardment (FAB), etc. The carboxypeptidase may act before or simultaneously with the ionization events. Subfragments are separated by mass by, e.g., magnetic sector, quadropole, ion cyclotron, or time-of-flight methods. For MS methods generally, see Siuzdak, G., *Mass Spectrometry for Biotechnology* (Academic Press 1996).

Since deuterium is not radioactive, the deuterium-labeled peptides must be identified by other means, such as mass spectrometry (their molecular weight will be greater than that of predicted for the same peptide without such a label).

If desired, the same binding protein: binding partner complex may be studied both by tritium exchange (which need only be to medium resolution) and by deuterium exchange. The tritium exchange method will identify the relevant fragments. Since the HPLC mobilities of these tritium-labeled fragments will then be known, the corresponding deuterium-labeled fragments can be identified by their common mobilities and then subfragmented, etc.

In a preferred embodiment, separate tritium and deuterium exchange runs are avoided. Instead, the deuterated water is supplemented with tritiated water, e.g. the solvent is 98% mole fraction deuterated water and 2% mole fraction tritiated water (e.g., 50 Ci/ml). As a result, the fragments are labeled both with deuterium and tritium, and the relevant fragments identified by their tritium-imparted radioactivity. The subfragments are still analyzed by mass spectroscopy for the presence of deuterated label (with appropriate correction for the relatively small amount of tritium also present). The purpose of the tritium is to radioactively tag peptide fragments containing binding surface residues. However, the exact residues involved are identified by MS analysis of deuterium bearing peptides that have been further digested with acid-reactive carboxypeptidases, allowing identification of the deuterated residues of the radioactive peptides.

In a preferred embodiment, receptor-binding partner complexes functionally labeled with deuterium and tritium at their interaction surface are (under slowed exchanged conditions as described above for high resolution tritium exchange analysis) pepsin digested, subjected to rpHPLC in 0.1% TFA-containing buffers and column effluent containing tritium labeled peptides subjected to mass spectroscopic analysis. To more precisely localize the deuterium label within each peptide, mass spectrometry is performed on labeled-proteolytic fragments, that are progressively further digested (under slowed exchange conditions) with acid reactive carboxypeptidases (41). This digestion can be performed before introduction of the sample into the mass spectrometer, or continuously in situ while the sample is held in the mass spectrometer. As digestion proceeds, molecular ions of each of the resulting enzyme-generated carboxy-terminal truncated peptide subfragments is detected by the mass spectrometer, and its molecular weight compared to that known for the undeuterated form of the same peptide fragment. Peptide fragments which bear functionally attached deuterium are identified by an increase in their molecular weight of one atomic unit when compared to the same peptide fragment generated from undeuterated receptor-binding partner. Sufficient subfragmentation and analysis as above results in the deduction of the protease-generated fragments that have functionally-bound deuterium. Thereby, the location of each deuterated amide within the peptide is determined.

In vivo Analysis

In situ analysis of protein-binding partner interactions is possible in vivo. The protein, while present in its native environment as a component of an intact living cell, or as a component of a cellular secretion such as blood plasma, is on-exchanged by incubating cells or plasma in physiologic buffers supplemented with tritiated (or deuterated) water. The binding partner is then added, allowed to complex to the cell or plasma-associated protein, and then off-exchange initiated by returning the cell or plasma to physiologic conditions free of tritiated (or deuterated) water. During the off-exchange period (hours to days) the formed protein-binding partner complex is isolated from the cell or plasma by any purification procedure which allows the complex to remain continuously intact. At the end of the appropriate off-exchange period, fragmentation and analysis of purified complex proceeds as above.

This analytic method is especially appropriate for proteins which lose substantial activity as a result of purification, as the binding site is labeled prior to purification.

Binding Site Analysis by Indirect Hydrogen Exchange

In the methods described above, the entire surface of the protein is labeled initially, and label is then removed from those surfaces which remain solvent exposed after formation of the complex of the binding protein and its binding partner. The binding site of the protein is occluded by the binding partner, and label is therefore retained at this site.

When the complex is formed, the binding protein may undergo changes in conformation (allosteric changes) at other sites, too. If these changes result in segments of the protein being buried which, previously, were on the surface, those segments will likewise retain label.

It is possible to distinguish binding site residues from residues protected from "off-exchange" by allosteric effects. In essence, the binding partner, rather than the binding protein, is labeled initially. The binding protein is labeled indirectly as a result of transfer of label from the binding partner to the binding protein. Such transfer will occur principally at the binding surface.

This procedure will functionally label receptor protein amides if they are slowed by complex formation and are also in intimate contact with the binding partner in the complexed state. Receptor protein amides that are slowed because of complex formation-induced allosteric changes in regions of the protein which are not near the protein-binding partner interaction surface will not be labeled. This procedure may be performed as follows:

1) binding partner is added to tritiated water (preferably of high specific activity) to initiate tritium exchange labeling of the binding partner.

2) After sufficient labeling is achieved, binding partner is separated from the excess of solvent tritium under conditions which produce minimal loss of tritium label from the binding partner. This can be accomplished by, e.g., a) shifting the buffer conditions to those of slowed exchange (0° C., acidic pH) followed by G-25 spin column separation of the binding partner into tritium-free buffer or b) employing stopped-flow techniques in which the on-exchange mixture is rapidly diluted with large volumes of tritium free buffer.

3) the tritium-labeled binding partner, now essentially free of excess solvent tritium, is added to receptor protein and conditions adjusted to allow spontaneous reversible (equilibrium) complex formation to take place between the two. The conditions of temperature and pH should also allow, and preferably maximize, the specific transfer of tritium label from the labelled binding partner to amides on the binding protein's interaction surface with partner. Typically, the pH will be 5–8 (conducive to ligand binding) and the temperature 0–37° C. Initially, use of pH 7 and 22° C. is recommended, the transfer being controlled by controlling the incubation time. A typical trial incubation time would be 24 hours. These conditions of pH, temperature and incubation time may of course be varied.

4) The complex is then incubated for periods of time sufficient to allow transfer of tritium label from the labeled binding partner to the receptor protein. During this incubation period, tritium which has on-exchanged to regions of the binding partner that are distant from the receptor-binding partner interaction surface will leave the binding partner by exchange with solvent hydrogen and be rapidly and highly diluted in the large volume of solvent water, thereby preventing its efficient subsequent interaction with the binding protein. However, tritium label that has been attached to binding partner amides present within the (newly formed) protein-binding partner interaction surface will be capable of exchanging off of the binding partner only during the brief intervals when the interaction surface is exposed to solvent water, i.e., when the complex is temporarily dissociated. When so dissociated and solvent exposed, a portion of tritium present on amides within the binding partner's interaction surface will leave the surface and for a brief time, remain within the proximity of the surface. Given the rapid (essentially diffusion limited) rebinding of binding protein and partner, much of the released tritium that (briefly) remains within the environs of the partner's binding surface will in part exchange with amides on the (future) interaction surface of the approaching binding protein molecule that subsequently binds to the binding partner. Once such binding occurs, the transferred tritium is again protected from exchange with solvent until the complex dissociates again. The result will be the progressive transfer of a portion of the tritium from the binding partner interaction surface to exchangeable amides on the cognate protein interaction surface.

Amides whose exchange rates are conformationally slowed each time complex formation occurs can also become labelled with tritium, but they will do so at a much slower rate than amides within the binding surface, as they are located more distant from the high concentration of tritium "released" at the interaction surface with each complex dissociation event. The efficiency of transfer is roughly inversely proportional to the cube of the distance between such conformational changes and the binding surface.

The binding protein-tritiated binding partner complex incubation conditions are adjusted to optimize specific interaction surface amide tritium transfer (SISATT) for a particular binding protein-partner pair. SISATT is defined as the ratio of the amount of tritium (CPM) transferred from binding partner to binding protein peptide amides previously determined (by the technique of claim 1) to undergo slowing of amide hydrogen exchange upon binding-protein partner complex formation divided by the total tritium (CPM) transferred from binding partner to all peptide amides in the binding protein.

5) After an incubation period that allows and preferably maximizes SISATT, the conditions of slow hydrogen exchange are restored, the complex is dissociated and the binding protein fragmented. Fragments of binding protein (as opposed to the initially labeled binding partner) that bear tritium label are identified, and further characterized as previously described. Alternatively, deuterium is used instead of tritium as the label. Deuterium has the advantage of allowing a much higher loading of label (since deuterium is much cheaper than tritium).

It is possible, also, to directly label the binding partner with deuterium and the binding protein with tritium. As a result, both the binding site and allosterically buried amides of the binding protein will be tritiated, but only binding site amides will be deuterated.

The indirect method is especially applicable to study of proteins which undergo substantial conformation of changes after, or in the course of binding, such as insulin and its receptor.

Compositions

After determining the binding sites of a binding protein or a binding partner, by the present methods (alone or in conjunction with other methods), the information may be exploited in the design of new diagnostic or therapeutic agents. Such agents may be fragments corresponding essentially to said binding sites (with suitable linkers to hold them in the proper spatial relationship if the binding site is discontinuous), or to peptidyl or non-peptidyl analogues thereof with the similar or improved binding properties. Or they may be molecules designed to bind to said binding sites, which may, if desired, correspond to the paratope of the binding partner.

The diagnostic agents may further comprise a suitable label or support. The therapeutic agents may further comprise a carrier that enhances delivery or other improves the therapeutic effect.

The agents may present one or more epitopes, which may be the same or different, and which may correspond to epitopes of the same or different binding proteins or binding partners.

EXAMPLE

As a demonstration of the practical use of this technology, Applicant has studied the interaction of human hemoglobin with two different monoclonal antibodies known to be reactive with defined and previously identified subregions of the hemoglobin binding protein haptoglobin. These studies employed monoclonal antibody β6-1-23456 (specific for the human hemoglobin β chain; epitope centered on or about β6-Glu and monoclonal antibody β-121 (specific for the human hemoglobin β chain in the region of residue β-121), both antibodies being the generous gift of C. R. Kiefer, Medical College of Georgia, Augusta, Ga. (51). Human haptoglobin was obtained from Calbiochem Corporation, La Jolla, Calif.

Preparation of hemoglobin: Blood was drawn from a normal donor into sodium heparin at 10 U/ml. Red blood cells were washed five times in cold phosphate buffered saline (PBS) (pH 7.4) with the buffy coat aspirated after each wash. An equal volume cold distilled water was added to the washed cell pellet to lyse cells, and then a one-half volume of cold toluene was added with vigorous vortexing. This mixture was centrifuged for 30 minutes in a cold Sorvall® centrifuge (Dupont) rotor at 15,000 rpm (33,000 g). The hemoglobin (middle) layer was removed and the centrifugation and hemoglobin decantation repeated. The isolated hemoglobin was dialyzed against four changes of cold 0.1M sodium phosphate, 0.5% NaCl pH 7.4. After dialysis, the sample was treated with carbon monoxide for 15 minutes. Final hemoglobin concentration was measured by using a molar extinction for heme at 540 nm of 14,270. The preparation was stored frozen in aliquots at −70° C.

Preparation of pepsin: Porcine pepsin (Worthington Biochemical Corp.) was dissolved at 10 mg/ml in 50 mM sodium acetate pH 4.5 and dialyzed against the same solution to remove proteolytic fragments. It was stored frozen in aliquots at −70° C.

Tritium exchange: All steps were performed at 0° C. On-exchange was initiated by mixing equal volumes (5 µl) of isolated hemoglobin (300 mg/ml) and tritiated water (50 Ci/ml) and the mixture incubated for four hours. Aliquots of this mixture (1.3 µl) were then added to equimolar quantities of either monoclonal β6, monoclonal β121, haptoglobin, (all at 10 mg/ml in PBS, pH 7.4, in a final incubation volume of 75 µl) or added to 75 µl of PBS alone. These hemoglobin-ligand mixtures were then immediately applied to 2 ml Sephadex® G-25 spin columns and centrifuged 4 minutes at 1100 g. Spin columns were prepared by filling 3 ml polypropylene columns (Fisher Scientific) with 2 ml of Sephadex G-25 fine equilibrated in PBS pH 7.4 plus 0.1% Triton® X-100. Columns were pre-spun at 1100 g for 2 minutes just before use. After column separation, samples were off-exchanged by incubation for a period of 40 hours, ten times the length of on-exchange. Samples were then hydrolyzed with pepsin. Typically, 25 µl of off-exchanged mixture containing 70 µg of hemoglobin was added to 10 µg pepsin in 110 µl of 0.1M $NaPO_4$ pH 2.7 plus 2.5 µl 0.5M $H_3PO_4$, the mixture incubated on ice for 10 minutes and then injected onto the HPLC column. An aliquot of on-exchanged hemoglobin was immediately adjusted to pH 2.7, passed over a pH 2.7 (0.1 M $NaPO_4$ pH 2.7) also proteolyzed and analyzed as above without a period of off-exchange. To measure on-exchange rates of specifically labeled amide protons, hemoglobin was on-exchanged as above but with time intervals ranging from 10 sec.–18 hours, reacted with ligand, and off-exchanged for 18 hours. Samples were then proteolyzed, subjected to HPLC as below, and specific label on peptides quantified as a function of on-exchange time.

High pressure liquid chromatography: Digested samples were analyzed on a Waters HPLC unit modified by putting the column and injector under melting ice. Mobile phase was prepared using Barnstead nanopure water, Aldrich ultrapure sodium phosphate, J. T. Baker Ultrex® grade HCL and HPLC grade acetonitrile from Burdick & Jackson. Mobile phase consisted of 50 mM $NaPO_4$ pH 2.7 (solvent A) and a mixture of 20% 50 mM $NaPO_4$ and 80% acetonitrile (ACN) final pH 2.7 (solvent B). Separation of peptides was achieved using a 30 cm Phenomenex Bondclone® 10 C18 column. The gradient program started at 100% A 0% B and altered the client to 83% A, 17% B over 3.4 minutes. From 3.4 to 6.7 minutes the system ran at a constant 83% A, 17% B and from 6.7 to 73.3 minutes the program implemented a linear increase in % B from 17% to 51%. Absorbance was monitored at 214 nm with a Waters model 441 detector.

For second dimension separation, peptide peaks bearing specific label isolated as were collected at 0° C., stored frozen at −70° C., thawed at 0° C., mixed with an equal volume of 100 mM $PO_4$ pH 2.7, and subjected to HPLC as above, except that buffer A was 0.115% trifluoracetic acid (TFA) in $H_2O$ and buffer B was 80% ACN, 20% $H_2O$, 0.1% TFA. Peaks bearing specific radiolabel were identified and isolated.

Sample collection: HPLC effluent was collected at the HPLC detector outflow with a Gilson model 203® fraction collector. Samples (100 to 400 fractions per run) were collected and radioactivity measured by adding five volumes of Aquamix (ICN Radiochemicals) followed by scintillation counting. In other studies, on-line liquid scintillation counting was performed using a B-RAM flow radiation detector (INUS Inc.).

Peptide identification: HPLC-isolated peptide were analyzed by both gas phase Edman sequencing and amino acid analysis at the UCSD protein sequencing facility.

Results

Hemoglobin-monoclonal Antibody Epitope Mapping

Figure 1B:
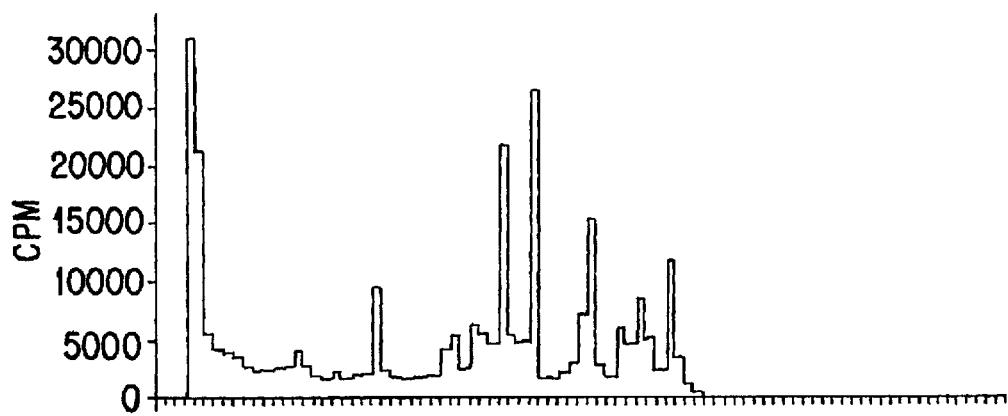
Figure 1C:
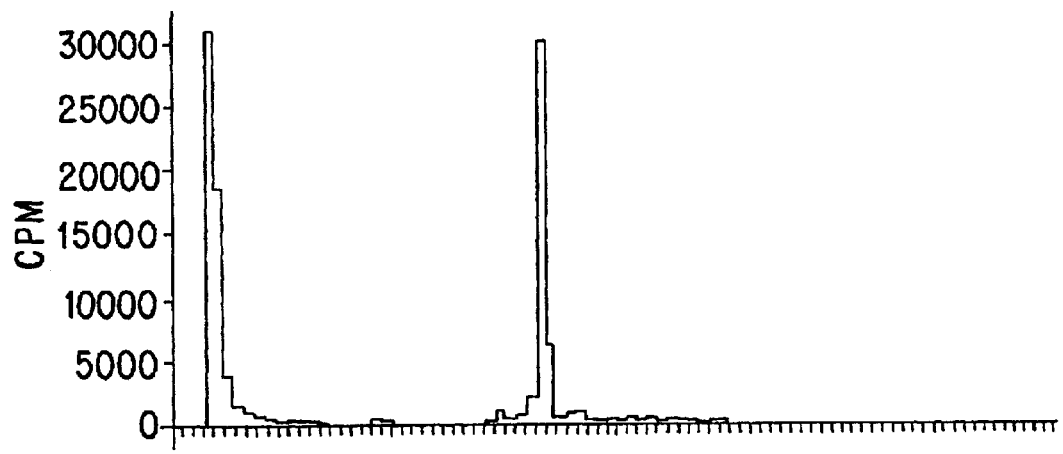
Figure 1D:
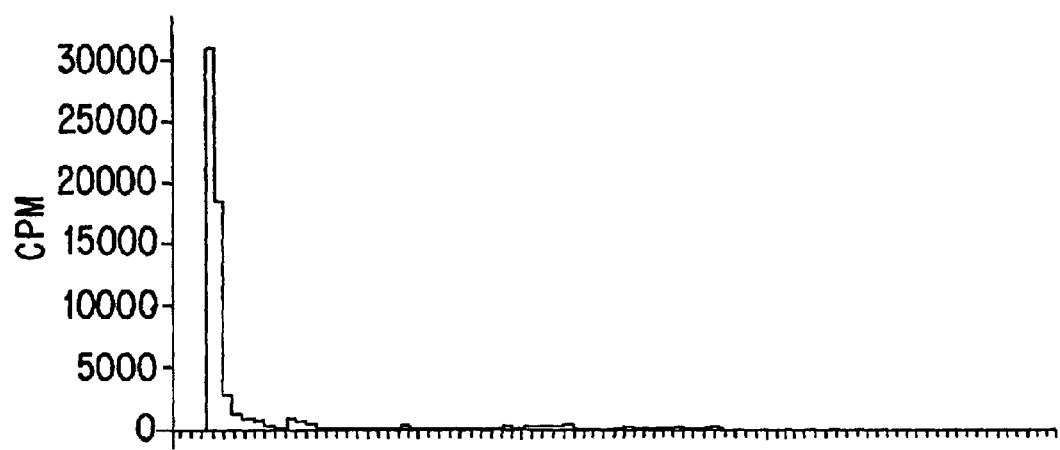

Hemoglobin was on-exchanged for 4 hours and then either proteolyzed without a period of off exchange (FIG. 1b), mixed with equimolar quantity of β6 monoclonal and then off-exchanged for 40 hours (FIG. 1c), mixed with monoclonal β-121 and off-exchanged for 40 hours (data not shown) or off-exchanged 40 hours in the absence of added antibody (FIG. 1d). When labeled hemoglobin is examined without a period of off exchange (FIG. 1b), at least 17 radiolabeled peaks were resolved, which generally corresponded to the peaks seen in the optical density trace of the same HPLC run (FIG. 1a). When labeled hemoglobin was allowed to fully off exchange without the presence of a protecting monoclonal antibody, all radiolabeled peaks disappeared (FIG. 1d). However, when labeled hemoglobin was off-exchanged in the presence of the β6 monoclonal, a single unique peak bearing radiolabel was seen indicating that this fraction contains the β6 monoclonal antigenic epitope (FIG. 1c).

Figure 2:
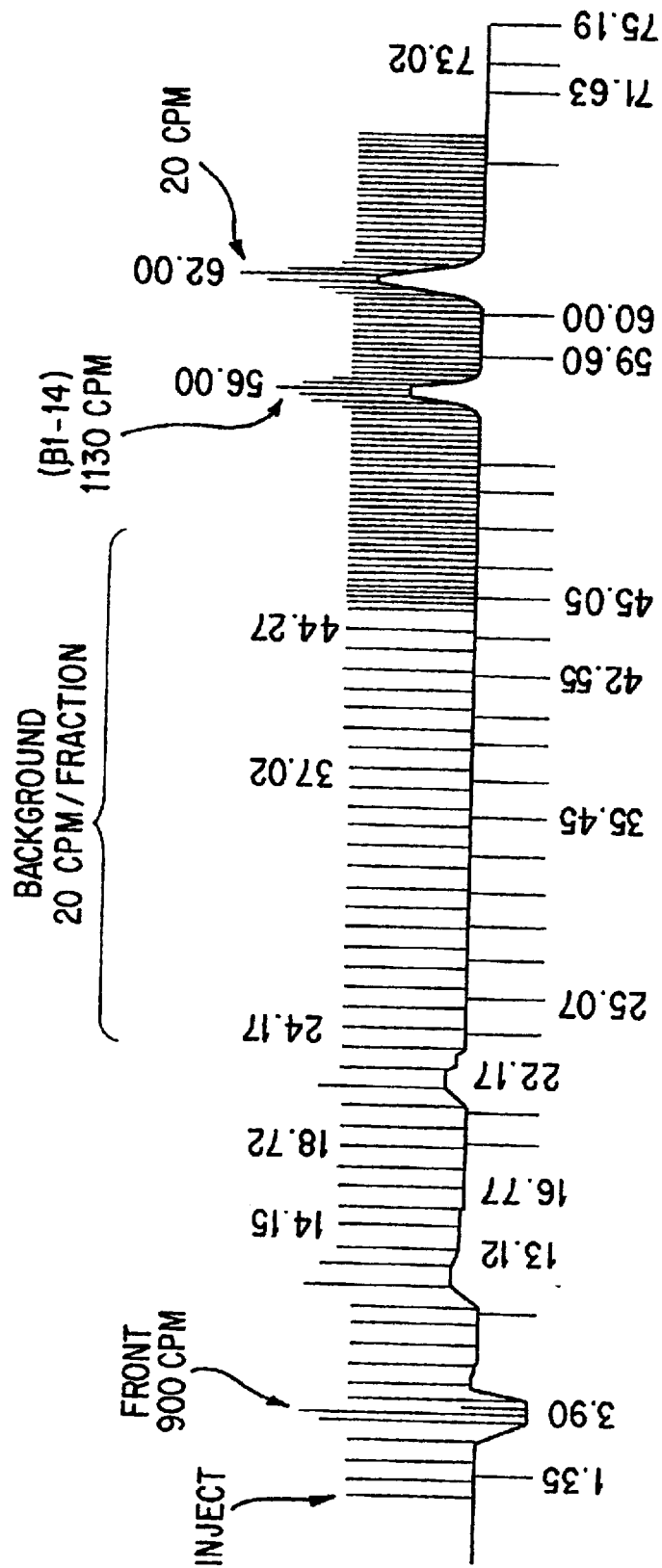
FIG. 2 depicts the results of second dimension separation (HPLC with 0.1% Trifluroracetic Acid (TFA) containing solvents) at 0° C. of tritium-bearing rpHPLC fraction from first dimension separation, FIG. 1c.

When this peak was subjected to second dimension HPLC in TFA-containing solvents under slowed proton exchange conditions, two peptides were resolved by optical density at 214 nm, with only one of these bearing radiolabel (see FIG. 2). This label-bearing peptide was found by gas phase microsequencing and amino acid analysis to represent residues 1–14 of the hemoglobin beta chain. Measurement of on-exchange rates of labeled amides in this peptide demonstrated two rate classes, both of equal size; one which exchanged on with a half life of less than 10 seconds, and another with a half life of approximately 1 hour. Specific activity measurements indicate that 4.3 amide protons within this 14-mer peptide are slowed by interaction of the β6 antibody with hemoglobin. A synthetic peptide identical to residues 1–14 of the hemoglobin β chain (β1–14) was synthesized, tritium labeled by proton exchange, and subjected to graded digestion with carboxypeptidase-P (see FIGS. 6a–j).

Figure 3A:
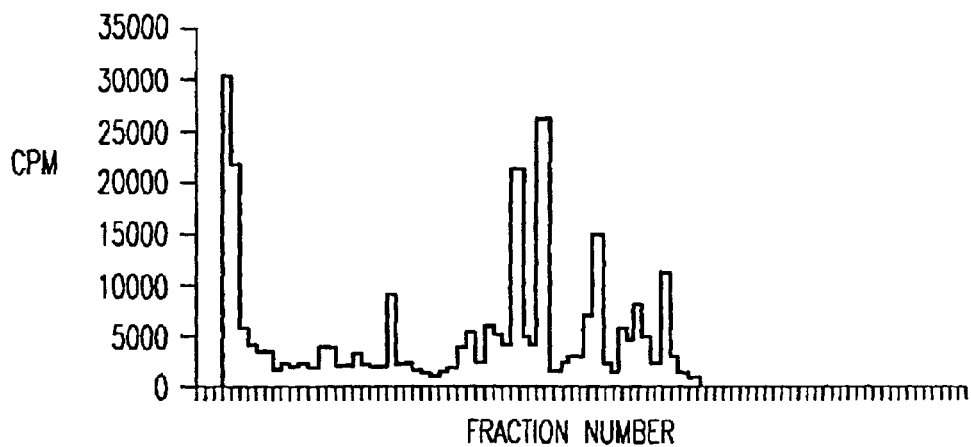
FIGS. 3a–c show the identification of hemoglobin peptides functionally labeled by interaction with monoclonal antibody β-121.
Figure 3B:
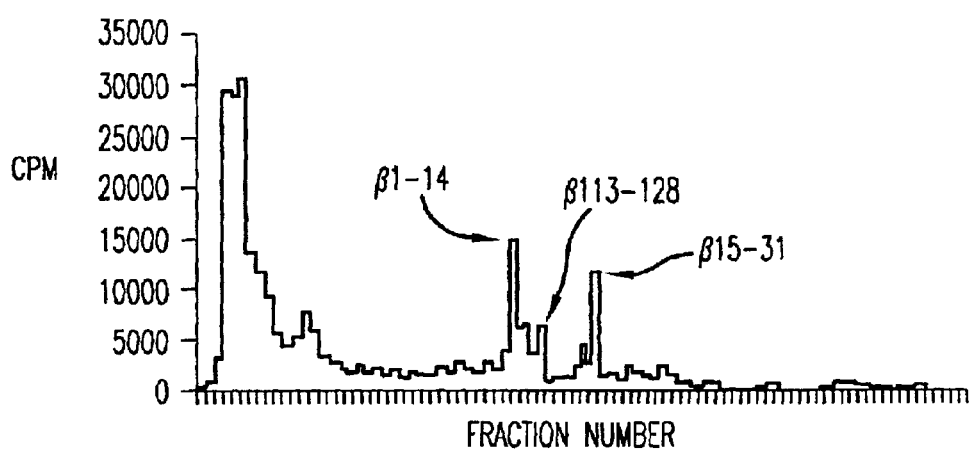
Figure 3C:
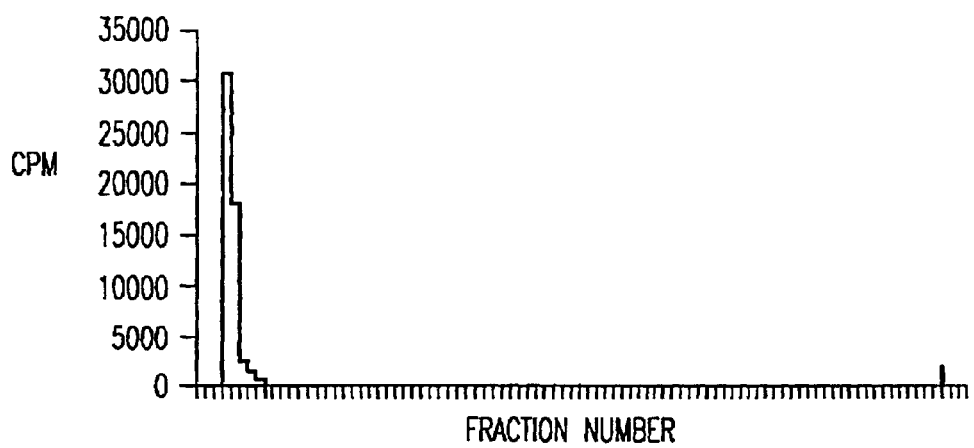

Similar studies were performed with hemoglobin off-exchanged after interaction with 0–121 monoclonal (FIGS. 3a–c). Three pepsin-generated peptides were found to bear tritium label (FIG. 3b). After second dimension HPLC separation in TFA-containing solvents these peaks were similarly resolved from contaminants, sequenced, and found to be hemoglobin polypeptides 1–14, β113–128, and β15–31. In preliminary proton counting studies, approximately two β121 monoclonal-slowed protons are present in each of these three peptides.

Figure 5A:
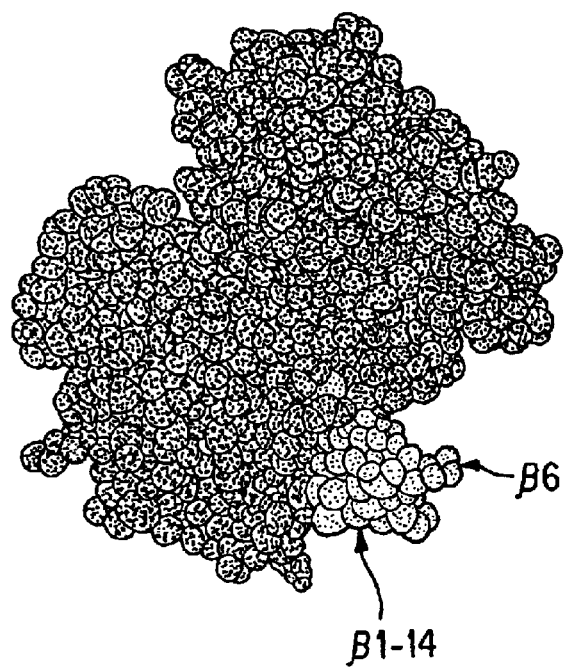
FIGS. 5a–b show the structure of hemoglobin with peptidic regions highlighted.
Figure 5B:
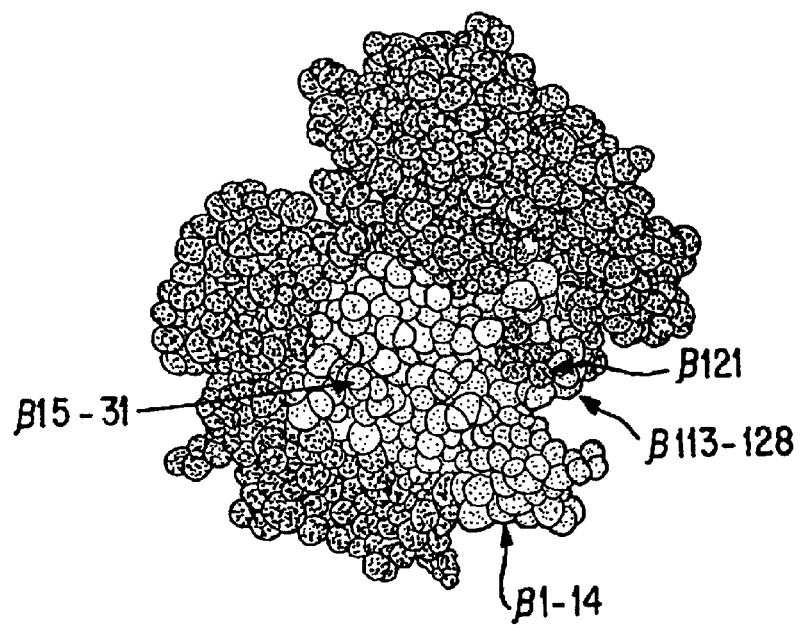
Figure 6A:
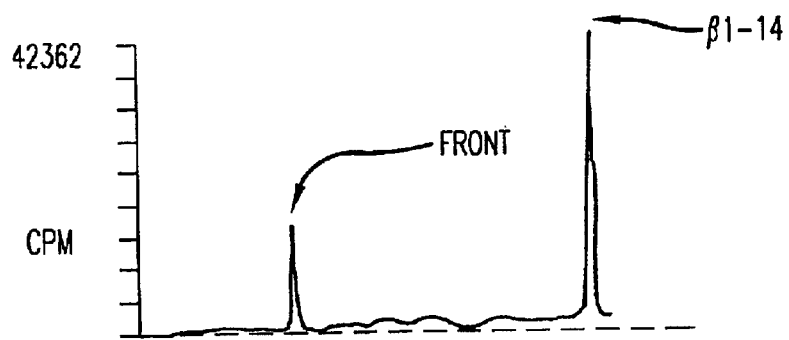
FIGS. 6a–j depict the results of carboxypeptidase-P digestion of β1–14 peptide. Tritium-exchange-labeled synthetic β1–14 peptide was digested (0° C.) with carboxypeptidase-P (CP-P) using a range of enzyme concentrations and digestion times as follows.
Figure 6B:
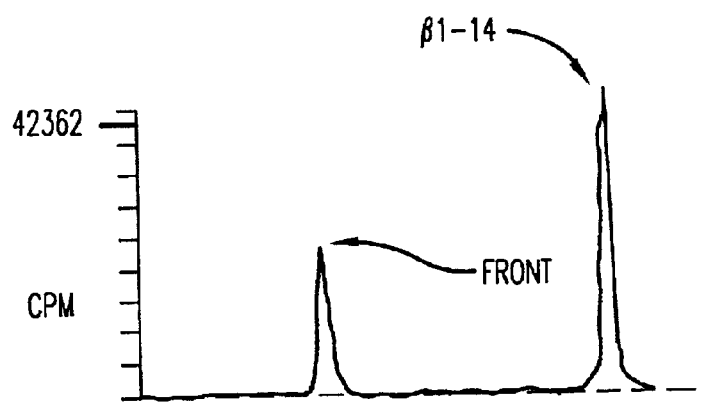
Figure 6C:
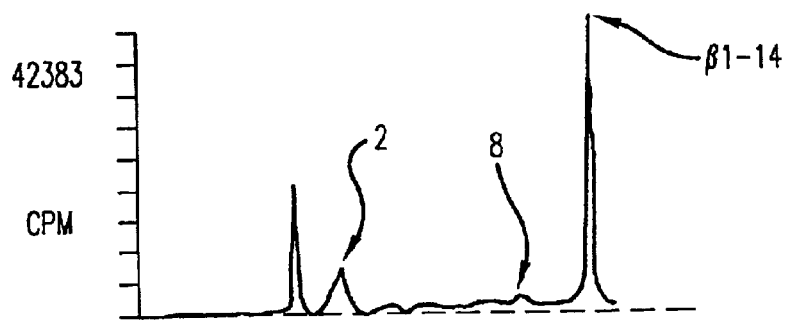
Figure 6D:
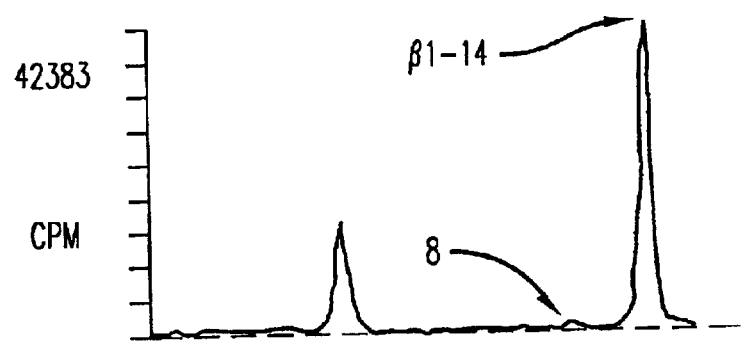
Figure 6E:
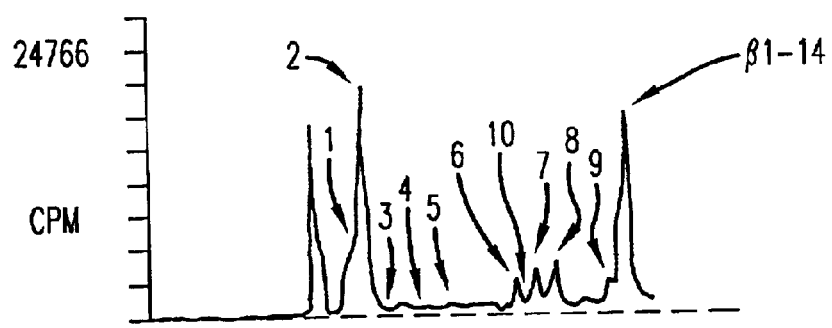
Figure 6F:
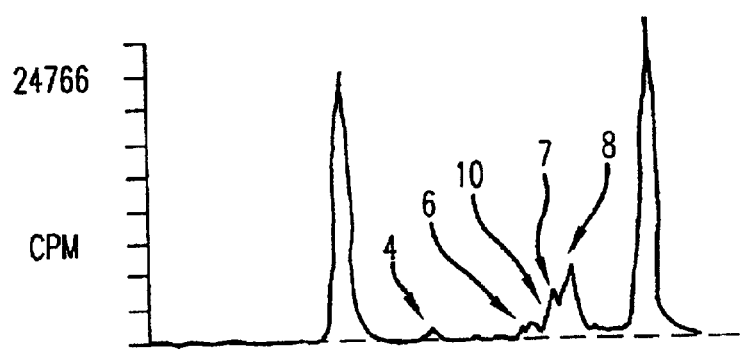
Figure 6G:
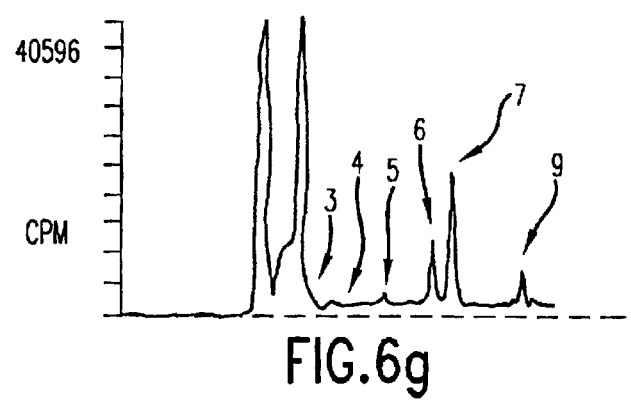
Figure 6H:
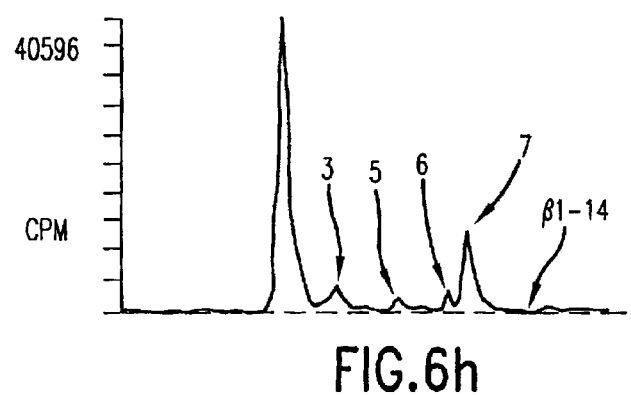
Figure 6I:
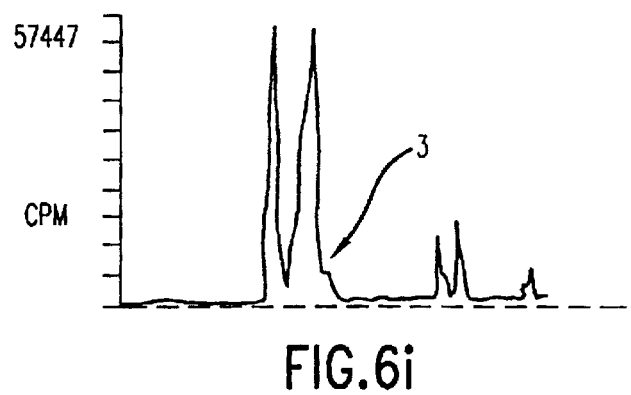
Figure 6J:
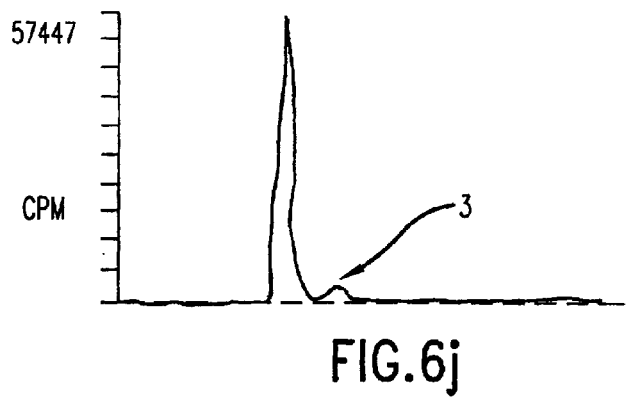
Figure 7A:
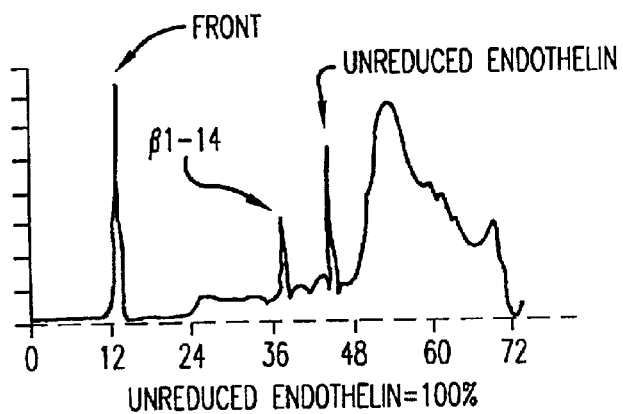
FIGS. 7a–j depict the results of reduction of disulfide bonds at pH 2.7. Tritium-exchange-labeled β1–14 peptide (2 μg at 0° C., pH 2.7) was supplemented with the peptide endothelin (4 μg), which contains two disulfide bonds (35), and the mixture incubated without (FIGS. 7a, 7b) or with (FIGS. 7c–j) 50 mM Tris (2-carboxyethyl) phosphine (TCEP) for varying times at 0° C.
Figure 7B:
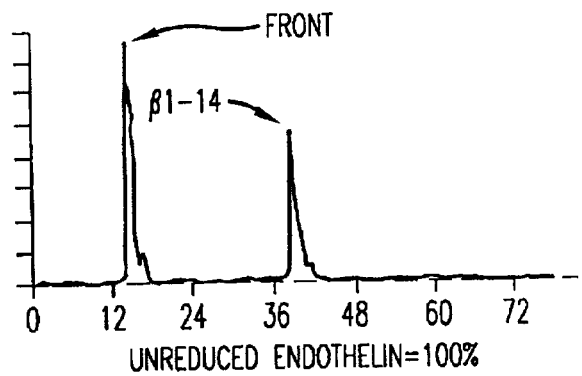
Figure 7C:
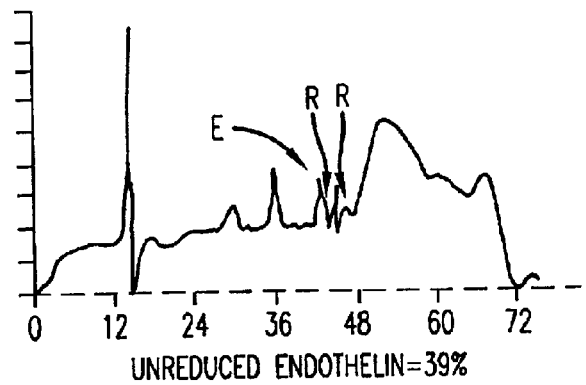
Figure 7D:
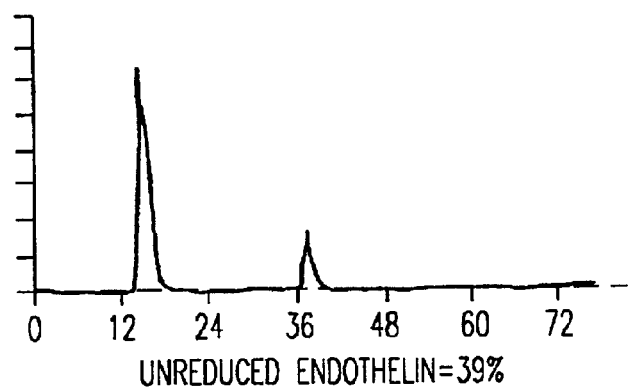
Figure 7E:
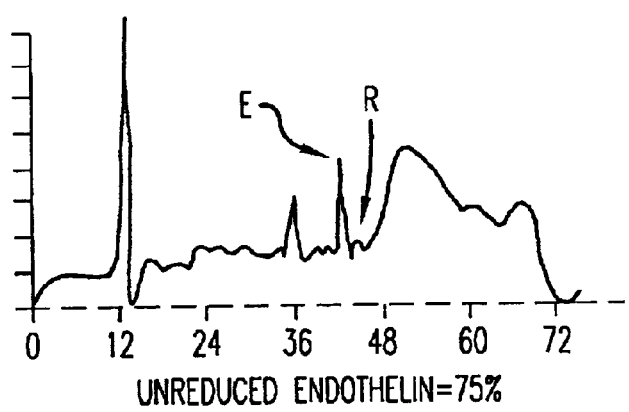
Figure 7F:
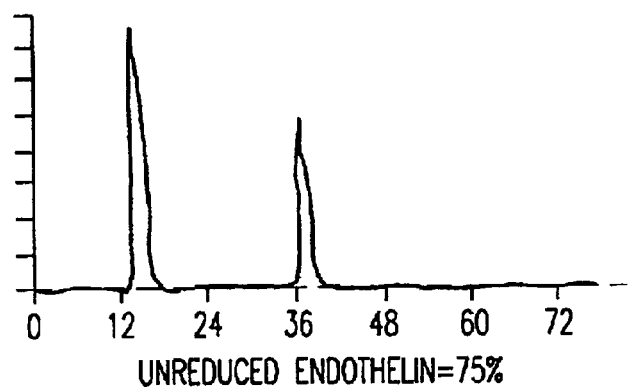
Figure 7G:
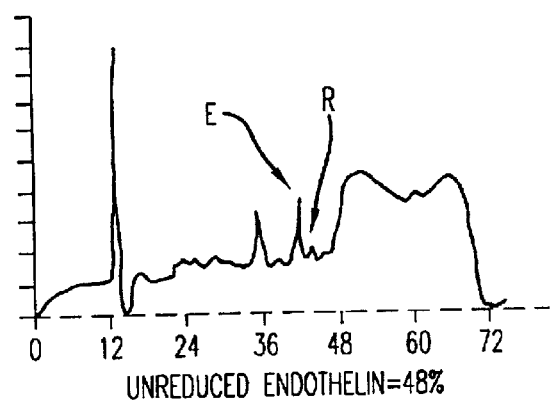
Figure 7H:
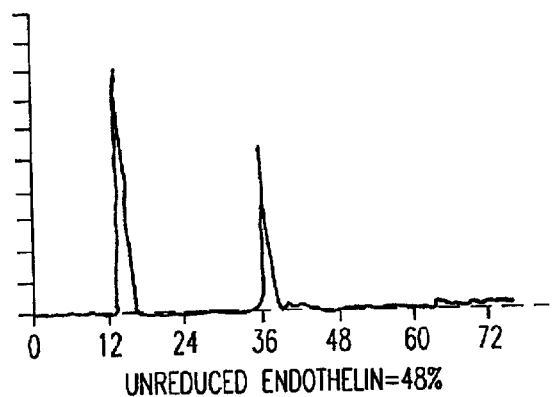
Figure 7I:
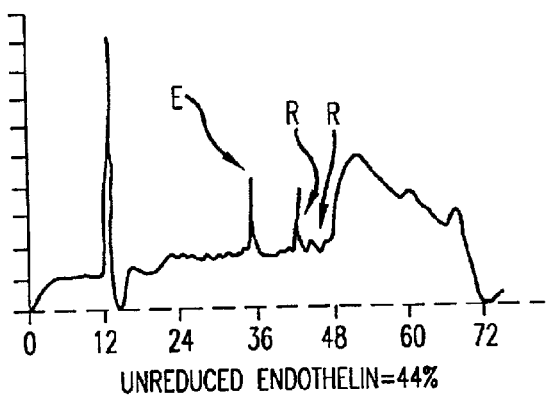
Figure 7J:
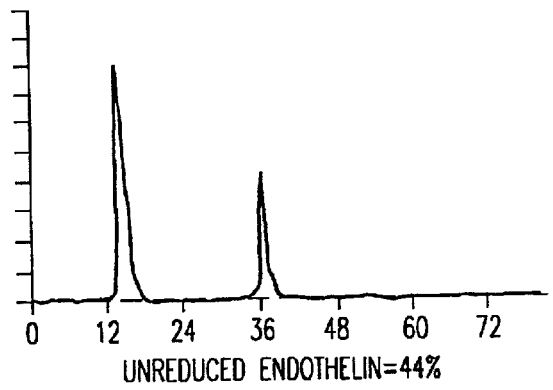

The position of these peptidic regions in the folded hemoglobin tetramer are shown in FIGS. 5a and 5b. The β6 monoclonal labels six amide bonds which are present on an externally disposed segment of the folded hemoglobin molecule (β chain amino acids 1–14) which includes the previously characterized target epitope of this monoclonal (β6–9) (51). The β-121 monoclonal labels a total of approximately six protons which, though present on the non-contiguous regions of the linear amino acid sequence of hemoglobin are seen to be surface disposed and located in close proximity to each other in the folded hemoglobin molecule, and include the hemoglobin β chain 121 residue.

Mapping of Hemoglobin-haptoglobin Interaction Sites

Figure 4A:
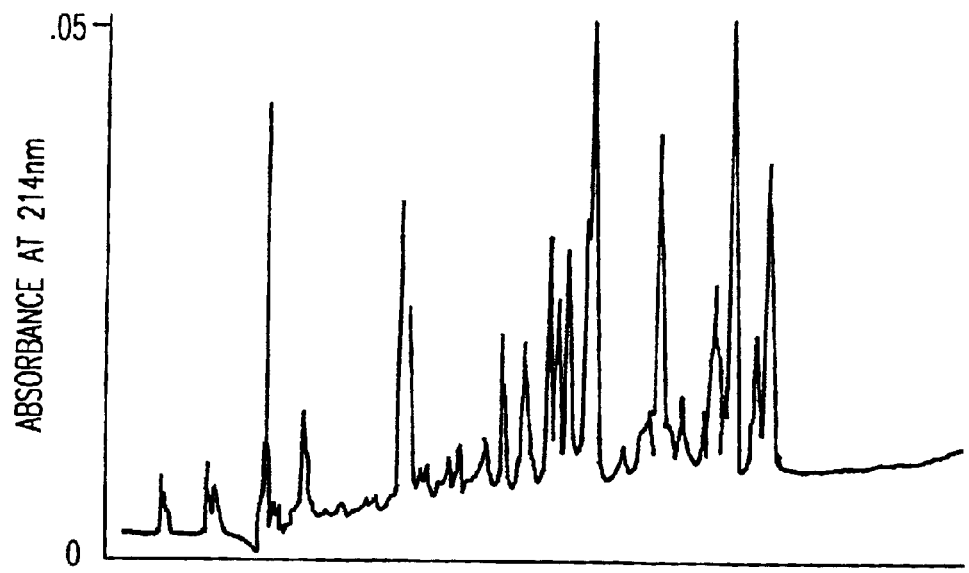
FIGS. 4a–d depict the identification of hemoglobin peptides functionally labeled by interaction with haptoglobin.
Figure 4B:
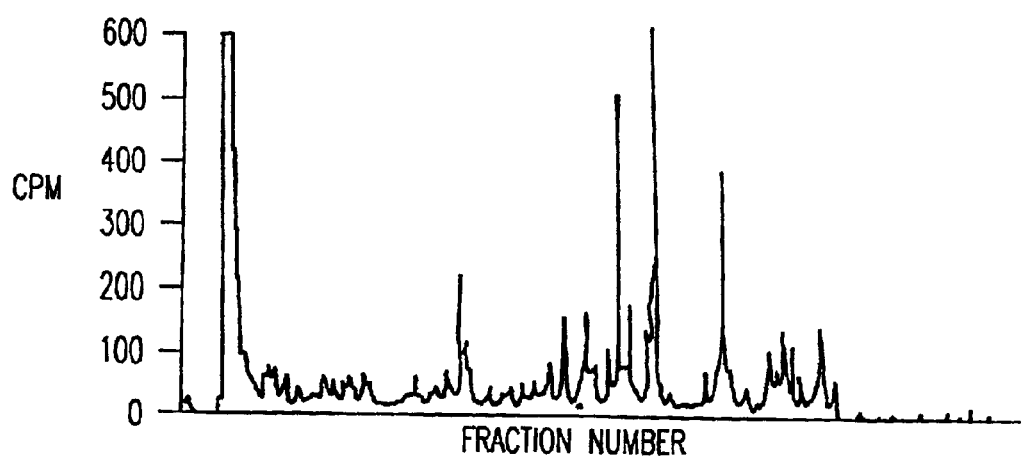
Figure 4C:
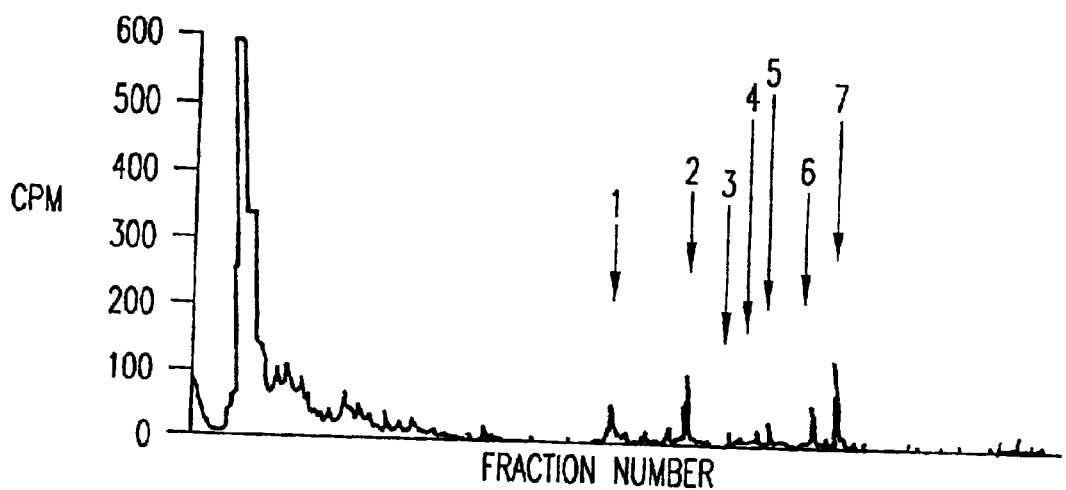
Figure 4D:
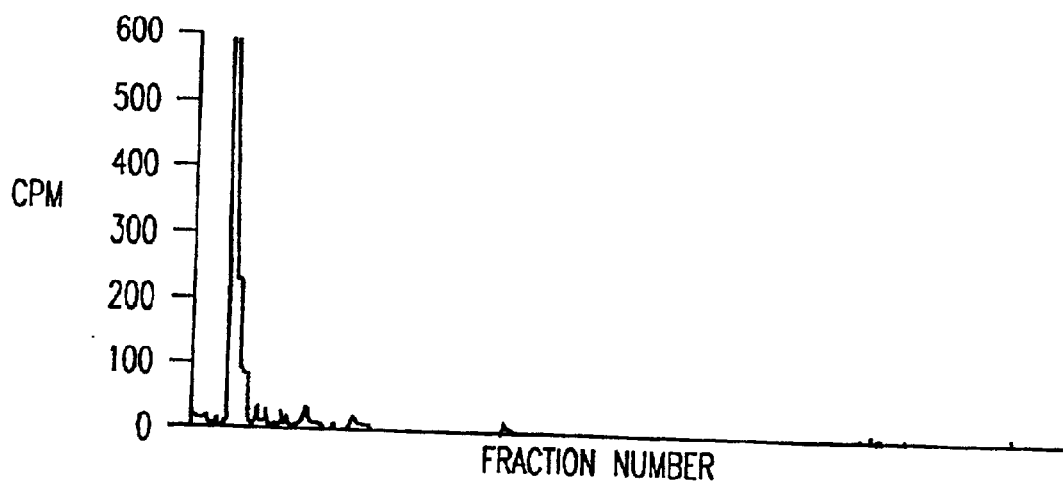

When hemoglobin binds to haptoglobin it is known that the hemoglobin molecule contacts haptoglobin through three non-contiguous peptidic regions which consist of hemoglobin a chain 121–127, β11–25 and β131–146 (52, 53). We therefore anticipated that pepsin cleavage of hemoglobin labeled at haptoglobin interaction sites would display between 2 and 10 radiolabeled peptides. We therefore performed our haptoglobin studies at a higher level of resolution, accomplished by collection of a larger number of HPLC fractions (see FIGS. 4a–d). Under these conditions, labeled hemoglobin analyzed without a period of off exchange demonstrates greater than 33 discernable radiolabeled peaks (FIG. 4b), which again correspond to the optical density tracing (FIG. 4a). Labeled hemoglobin off-exchanged in the presence of haptoglobin produces 7 specifically radiolabeled peaks (FIG. 4c) which are not present if hemoglobin is off-exchanged in the absence of haptoglobin (FIG. 4d). These results indicate that this technology works well with a receptor-like ligand interaction system as complex as that of hemoglobin with haptoglobin.

Solvent Effect

Synthetic hemoglobin β1–14 peptide was tritium-labeled at all peptide amides by proton exchange, and aliquots of labeled peptide subjected to 0° C. HPLC analysis as in FIGS. 1a–d except that a range of solvent pH's were utilized as indicated below. The percent of original peptide-bound tritium that remained bound to the peptide under each HPLC condition was then determined.

| pH | A solvent | B solvent |
|---|---|---|
| 2.1 | 0.115% TFA in water | 80% ACN, 20% $H_2O$, 0.1% TFA |
| 2.7 | 50 mM $PO_4$, pH 2.7 | 80% ACN, 20% 50 mM $PO_4$, pH 2.7 |
| 3.5 | 50 mM $PO_4$, pH 3.5 | 80% ACN, 20% 50 mM $PO_4$, pH 3.5 |
| 4.0 | 50 mM $PO_4$, pH 4.0 | 80% ACN, 20% 50 mM $PO_4$, pH 4.0 |

Tritium retention was about 57% for TFA (pH 2.1), 46% for $PO_4$ (pH 2.7), 34% for $PO_4$ (pH 3.5), and 14% for $PO_4$ (pH 4.0).

The invention is not to be limited in scope by the specific embodiments described which are intended as single illustrations of individual aspects of the invention, and functionally equivalent methods and components are within the scope of the invention. Indeed, various modifications of the invention, in addition to those shown and described herein, will become apparent to those skilled in the art from the foregoing description and accompanying drawings. Such modifications are intended to fall within the scope of the appended claims.

All references cited herein are incorporated in their entireties by reference for all purposes.

REFERENCES

1. Horsfall, A. C., et al., Epitope mapping. *Immunology Today* 12:211–213, 1991.
2. Arnon, R., et al., Structural basis of antigenic specificity and design of new vaccines. *FASEB J* 6:3265–3274, 1992.
3. Englander, S. W., et al., The assignment of proton resonances in 2D NMR spectra of proteins. *Techniques in Protein Chemistry*, TE Hughim ed. Academic Press, San Diego, pg 207–222, 1989.
4. Englander, S. W., et al., Hydrogen-Tritium exchange. *Methods in Enzymology* 49:24–39, 1978.
5. Englander, S. W., et al., Hydrogen-tritium exchange. *Methods in Enzymology* 26:406–413, 1972.
6. Englander, J. J., et al., Protein hydrogen exchange studied by the fragment separation method. *Analytical Biochemistry* 147:234–244, 1985.
7. Englander, S. W., et al., Hydrogen-tritium exchange of the random chain polypeptide. *Biopolymers* 7:379–393, 1969.
8. Molday, R. S., et al., Primary structure effects on peptide group hydrogen exchange. *Biochemistry* 11:150, 1972.
9. Kim, P. S., et al., Influence of charge on the rate of amide proton exchange. *Biochemistry* 21:1, 1982.
10 Bai, Y., et al., Primary structure effects on peptide group hydrogen exchange. *Proteins: Structure, Function, and Genetics* 17:75–86, 1993.
11. Connelly, G. P., et al., Isotope effects in peptide group hydrogen exchange. *Proteins: Structure, Function, and Genetics* 17:87–92, 1993.

12. Englander, S. W., et al., Hydrogen exchange studies or respiratory proteins. III. Structural and free energy changes in hemoglobin by use of a difference method. *J. Biol. Chem.* 248:4852–4861, 1973.
13. Englander, J. J., Hydrogen-tritium exchange survey of allosteric effects in hemoglobin. *Biochemistry* 26:1846–1850, 1987.
14. Louie, G., et al., Salt, phosphate and the Bohr effect at the haemoglobin beta chain C terminus studied by hydrogen exchange. *J. Mol. Biol.* 201:765–772, 1988.
15. Rosa, J. J., et al., An experimental procedure for increasing the structural resolution of chemical hydrogen-exchange measurements on proteins: Application to ribonuclease S peptide. *J. Mol. Biol.* 133:399–416, 1979.
16. Rosa, J. J., et al., Hydrogen exchange from identified regions of the S-protein component of ribonuclease as a function of temperature, pH, and the binding of S-peptide. *J. Mol. Biol.* 145:835–851, 1981.
17. Rosa, J. J., et al., Effects of binding of S-peptide and 2'-cytidine monophosphate on hydrogen exchange from the S-protein component of ribonuclease S. *J. Mol. Biol.* 160:517–530, 1982.
18. Englander, S. W., et al., Individual breathing reactions measured in hemoglobin by hydrogen exchange methods. *Biophys. J.* 10:577, 1979.
19. Rogero, J. R., et al., Individual breathing reactions measured by functional labeling and hydrogen exchange methods. *Methods in Enzymology* 131:508–517, 1986.
20. Ray, J., et al., Allosteric sensitivity in hemoglobin at the a-subunit N-terminus studied by hydrogen exchange. *Biochemistry* 25:3000–30007, 1986.
21. Louie, G., et al., Allosteric energy at the hemoglobin beta chain C terminus studied by hydrogen exchange. *J. Mol. Biol.* 201:755–764, 1988.
22. Burz, D. S., et al., Mapping structure perturbation in *Escherichia coli* aspartate transcarbamylase by medium resolution hydrogen exchange. *Biophys. J.* 49:70–72, 1986.
23. Mallikarachchi, D., et al., Effects of ATP and CTP on the conformation of the regulatory subunit of *Escherichia coli* aspartate transcarbamylase in solution: A medium-resolution hydrogen exchange study. *Biochemistry* 28:5386–5391, 1989.
24. Beasty, A. M., et al., Characterization of an early intermediate in the folding of the a subunit of tryptophan synthase by hydrogen exchange measurement. *Biochemistry* 24:3547–3553, 1985.
25. Fromajeot, et al., U.S. Pat. No. 3,828,102. Method for preparation of tritium labeled proteins. Filed Sep. 19, 1972, issued August 1974.
26. Benson. U.S. Pats. No. 3,560,158 and 3,623,840. Method for analysis of labile hydrogen containing compounds. Filed Aug. 12, 1965, issued Feb. 2, 1971.
27. Fesik, et al., *Biochem Biophys Res Comm* 147 (3):892–898, 1987.
28. Paterson, Y., et al., An antibody binding site on cytochrome c defined by hydrogen exchange and two-dimensional NMR. *Science* 249:755–759, 1990.
29. Mayne, L., et al., Effect of antibody binding on protein motions studied by hydrogen-exchange labeling and two-dimensional NMR. *Biochemistry* 31:10678–10685, 1992.
30. Benjamin, D.C., et al., Long-range changes in a protein antigen due to antigen-antibody interaction. *Biochemistry* 31:9539–9545, 1992.
31. Ruegg, Uth, et al., Reductive cleavage of cystine disulfides with tributyl phosphine. *Meth Enzymol* 47:111–117, 1977.
32. Kirley, T. L., Reduction and fluorescent labeling of cyst(e)ine-containing proteins for subsequent structural analyses. *Anal Biochem* 180:231, 1989.
33. Burns, J. A., et al., Selective reduction of disulfides by Tris (2-carboxyethyl) phosphine. *J Org Chem* 56:2648–2650, 1991.
34. Levison, M. E., et al., Reduction of biological substances by water-soluble phosphines: Gamma globulin (IgG). *Experientia* 25:126–127, 1969.
35. Gray, W. R., Disulfide structures of highly bridged peptides: A new strategy for analysis. *Protein Science* 2:1732–1748, 1993.
36. Gray, W. R., Echistatin disulfide bridges: Selective reduction and linkage assignment. *Protein Science* 2:1479–1755, 1993.
37. Takayuki, T., et al., Cathepsin D from porcine and bovine spleen. *Methods in Enzymology* 80:565–581, 1981.
37a. Krishnan, S., et al., Purification of an acid protease and a serine carboxypeptidase from *Aspergillus niger* using metal-chelate affinity chromatography. *J Chromatography* 329:165–170, 1985.
37b. Xiaoming, L., et al., A novel carboxylesterase from *aspergillus niger* and its hydrolysis of succinimide esters. *Carlsberg Res Commun* 54:241–249, 1989.
37c. Zhu, H., et al., Purification and characterization of an extracellular acid proteinase from the ectomycorrhizal fungus *Hebeloma crustuliniforme*. *Applied Environmental Microbiology* 56:837–843, 1990.
38. Fusek, M., et al., Enzymic properties of thermopsin. *J Biol Chem* 265:1496–1501, 1990.
39. Breddam, K. Serine carboxypeptidases. A review. *Carlsberg Res Commun* 51:83–128, 1986.
40. Tsugita, A., Developments in protein microsequencing. *Adv Biophys* 23:81–113, 1987.
40a. Byrne, R. H., et al., An improved freeze-drying technique for the study of hydrogen exchange of proteins and polypeptides. *Analytical Biochemistry* 33:414–428, 1970.
40b. Schreier, A. A., et al., Concentration-dependent hydrogen exchange kinetics of $^3$H-labeled S-peptide in ribonuclease S. *J Mol Biol* 105:409–426, 1976.
41. Smith, C. E., et al., Carboxy-terminal protein sequence analysis using carboxypeptidase P and electrospray mass spectrometry. *Techniques in Protein Chemistry IV*, pg 463, 1993.
42. Rosuack, K. J., et al., C-terminal sequencing of peptides using electrospray ionization mass spectrometry. *Rapid Communications in Mass Spectrometry* 6:637–640, 1992.
43. Loo, J. A., et al., Primary sequence information from intact proteins by electrospray ionization tandem mass spectrometry. *Science* 248:201–204, 1990.
44. McCloskey, J. A., Introduction of deuterium by exchange for measurement by mass spectrometry. *Methods in Enzymology* 193:329–338, 1990.
45. Thevenon-Emeric, G., et al., Determination of amide hydrogen exchange rates in peptides by mass spectrometry. *Anal Chem* 64:2456–2458, 1992.
46. Winger, B. E., et al., Probing qualitative conformation differences of multiply protonated gas-phase proteins via H/D isotopic exchange with $D_2O$. *J Am Chem Soc* 114:5897–5989, 1992.
47. Zhang, Z., et al., Determination of amide hydrogen exchange by mass spectrometry: A new tool for protein structure elucidation. *Protein Science* 2:522–531, 1993.
48. Katta, V., et al., Hydrogen/Deuterium exchange electrospray ionization mass spectrometry: A method for probing protein conformational changes in solution. *J Am Chem Soc* 115:6317–6321, 1993.

49. Chi, H. T., et al., Use of deuterium-hydrogen exchange to characterize the fragmentation pathways of arteether and its metabolites in a thermospray mass spectrometer. *Organic Mass Spectrometry* 28:17–17, 1993.
50. Sepetov, N. F., et al., The use of hydrogen-deuterium exchange to facilitate peptide sequencing by electrospray tandem mass spectrometry. *Rapid Communication in Mass Spectrometry* 7:58–62, 1993.
51. Kiefer, C. R. et al., Negative screening for sickle cell diseases with a monoclonal immunoassay on newborn blood eluted from filter paper. *J. Lab. Clin. Med.* 116:826–830, 1990.
52. Yoshioka, N. et al., Haemoglobin binding with haptoglobin. *Biochem. J.* 234:453–456, 1986.
53. McCormick, D. J., et al., Hemoglobin binding with haptoglobin: Delineation of the haptoglobin binding site on the a-chain of human hemoglobin. *J. Protein Chem.* 9:735, 1990.
54. Tsugita, A. et al., Reaction of pentafluoropropionic anhydride vapor on polypeptide as revealed by mass spectrometry. A carboxypeptidase mimetic degradation. *Chemistry Letters* 235–238, 1992.
55. Tsugita, A., et al., Development of novel c-terminal sequencing methods. *Methods in Protein Sequence Analysis*, edited by K Imahori, F Sakiyama, Plenum Press, New York, 1993, pp. 55.

What is claimed is:

1. A method of characterizing a binding site of a binding protein of known or determinable amino acid sequence, said method comprising the steps of:
   (a) selectively labeling peptide amide groups in a binding site of the binding protein that have been determined to be substantially protected from exchange with solvent hydrogens in a situation where the binding protein binds its binding partner;
   (b) progressively degrading, under conditions of slow hydrogen exchange, the selectively labeled binding protein to obtain at least one series of subfragments, wherein each subfragment of each of said series is shorter than the preceding subfragment in the series by about 1–5 fewer amino acid residues at one terminus;
   (c) quantifying an amount of heavy hydrogen on each subfragment; and
   (d) correlating the amount of label on the subfragments with the amino acid sequence of the binding protein, thereby localizing the positions of the binding protein that had been labeled to within about 1–5 amino acid residues and thus characterizing the binding site of the binding protein.

2. A method of characterizing a binding site of a binding protein of known or determinable amino acid sequence, said method comprising the steps of:
   (a) selectively labeling peptide amide groups in a binding site of the binding protein so as to obtain a selectively labeled binding protein wherein either (i) the solvent inaccessible peptide amide groups of the binding protein comprise a heavy hydrogen and the solvent accessible peptide amide groups comprise a normal hydrogen or (ii) the solvent inaccessible peptide amide groups of the binding protein comprise a normal hydrogen and the solvent accessible peptide amide groups comprise a heavy hydrogen, and wherein the solvent inaccessible peptide amide groups have been determined to be those groups that are substantially inaccessible to solvent in a situation where the binding protein binds its binding partner;
   (b) fragmenting the selectively labeled binding protein into a plurality of fragments under conditions of slow hydrogen exchange;
   (c) determining which fragments are labeled with heavy hydrogen;
   (d) progressively degrading, under conditions of slow hydrogen exchange, each of the heavy hydrogen-labeled fragments to obtain at least one series of subfragments, wherein each subfragment of each of said series is shorter than the preceding subfragment in the series by about 1–5 fewer amino acid residues at one terminus;
   (e) quantifying an amount of heavy hydrogen on each subfragment; and
   (f) correlating the amount of heavy hydrogen on the subfragments with the amino acid sequences of the fragments from which the subfragments were generated, thereby localizing the positions of the fragment that had been labeled with heavy hydrogen to a resolution about 1–5 amino acid residues, and thus characterizing the binding site of the binding protein.

3. The method of claim 1 or 2 wherein the selectively labeling peptide amide groups of the binding protein comprises the steps of:
   (i) contacting the binding protein with a binding partner under conditions wherein the binding protein binds the binding partner so as to form a binding protein-binding partner complex; and
   (ii) contacting the complex with a heavy hydrogen-labeled solvent under conditions of rapid hydrogen exchange for an "on-exchange" period sufficient for solvent-accessible peptide amide hydrogens of the complex to exchange with, and be substantially replaced by, heavy hydrogens of the solvent, in a detectable number of molecules of the complex.

4. The method of claim 1 or 2 wherein the selectively labeling peptide amide groups of the binding protein comprises the steps of:
   (i) contacting the binding protein with a heavy hydrogen-labeled solvent under conditions of rapid hydrogen exchange for an "on-exchange" period sufficient for solvent-accessible peptide amide hydrogens of the binding protein to exchange with, and be substantially replaced by, heavy hydrogens of the solvent, in a detectable number of molecules of the binding protein;
   (ii) contacting the binding protein with a binding partner under conditions wherein the heavy hydrogen labels are substantially retained and wherein the binding protein binds the binding partner so as to form a binding protein-binding partner complex; and
   (iii) contacting the complex with a solvent that is substantially free of heavy hydrogen under rapid exchange conditions for an "off-exchange" period sufficient for solvent-accessible peptide amide hydrogens or heavy hydrogens of the complex to exchange with, and be substantially replaced by, normal hydrogen of the solvent.

5. The method of claim 4 wherein the heavy hydrogen is tritium and wherein said quantifying step comprises radioactivity measurements.

6. The method of claim 4 wherein the heavy hydrogen is deuterium and wherein said quantifying step comprises measuring the mass of the fragment or subfragment.

7. The method of claim 2, further including the step of separating the fragments prior to determining which fragments are labeled with heavy hydrogen.

8. The method of claim 7 in which the separation comprises two sequential separations steps which are carried out under different conditions.

9. The method of claim 8 in which the first sequential separation step is carried out at a pH in the range of pH 2.1 to pH 3.0 and the sequential separation is carried out at a pH in the range of pH 2.1 to pH 3.0, where the pH of the first and second sequential separation steps are different.

10. The method of claim 9, in which the first sequential separation step is carried out at a pH of 2.7 and the second sequential separation step is carried out at a pH of 2.1.

11. The method of claim 4 in which the degradation of the selectively labeled binding protein or labeled fragments comprises contacting the selectively labeled binding protein or labeled fragments with an acid resistant carboxypeptidase selected from the group consisting of carboxypeptidase P, carboxypeptidase Y, carboxypeptidase W and carboxypeptidase C.

12. The method of claim 4 further comprising disrupting any disulfide bridges in the selectively labeled binding protein under conditions of slow hydrogen exchange prior to said fragmenting or said progressively degrading.

13. The method of claim 12 wherein said disrupting is carried out by contacting the selectively labeled binding protein with a water-soluble phosphine at 0–10° C.

14. The method of claim 4 further comprising, prior to fragmenting or progressively degrading, denaturing the selectively-labeled binding protein under con of slow hydrogen exchange.

15. The method of claim 14 in which the denaturing is carried out in a solvent such that the pH for minimization of hydrogen exchange is substantially higher than that of a purely aqueous solution.

16. The method of claim 15 in which the solvent comprises about 5–20% water and the remainder is a nonaqueous polar solvent.

17. The method of claim 16 in which the nonaqueous polar solvent is selected from the group consisting of acetonitrile, dimethyl sulfoxide, a polyol and combinations thereof.

18. The method of claim 17 in which the polyol is glycerol.

19. The method of claim 16 in which the solvent further includes about 2–4 M guanidine thiocyanate.

20. The method of claim 16, wherein the pH of the solvent is pH 4.8–5.2.

21. The method of claim 1 or 2 wherein each of said series of subfragments comprises a mixture in which each subfragment is present in an analytically sufficient quantity to permit its identification.

22. The method of claim 1 or 2 wherein said progressively degrading is carried out contemporaneously with said quantifying step.

23. A method of determining, at a resolution of about 1–5 amino acid residues, the position of a peptide amide group labeled with a heavy hydrogen in a binding site of a binding protein of known or determinable amino acid sequence, said method comprising the steps of:

(a) selectively labeling peptide amide groups in a binding site of the binding protein that have been determined to be substantially protected from exchange with solvent hydrogens in a situation where the binding protein binds its binding partner;

(b) progressively degrading, under conditions of slow hydrogen exchange, said binding protein into a mixture of subfragments, wherein said mixture comprises at least one series of subfragments, such that each subfragment in each of said series is shorter than the preceding subfragment in the series by about 1–5 amino acid residues at one terminus and such that the first subfragment in the series is derived from and composed of about 1–5 fewer amino acid residues than said protein and such that the last subfragment in the series is about 1–5 amino acid residues in length; and, when said mixture of subfragments comprises an analytically sufficient quantity of each subfragment in each of said series, (c) quantifying an amount of heavy hydrogen label on each subfragment; and (d) correlating the amount of heavy hydrogen label of each subfragment with the amino acid sequence of the binding protein, thereby localizing the position of the labeled peptide amide group in the binding site of the binding protein to within about 1–5 amino acid residues.

24. The method of claim 1 or 2 wherein said fragmenting is achieved by use of an acid tolerant protease from the Aspergillus protease family.

25. The method of claim 2 wherein the heavy hydrogen label is tritium and wherein said determining comprises radioactivity measurements.

26. The method of claim 2 wherein the heavy hydrogen label is deuterium and wherein said determining comprises measuring the mass of the subfragment.

* * * * *